US012225936B2

(12) United States Patent
Noori et al.

(10) Patent No.: US 12,225,936 B2
(45) Date of Patent: Feb. 18, 2025

(54) DISPOSABLE CAPSULE FOR THE EFFICIENT GENERATION OF HERBAL VAPOR WITH VAPOR PRODUCING DEVICES

(71) Applicants: 2334271 ONTARIO LIMITED, Ontario (CA); Nariman Keramati Noori, Stuttgart (DE); Clemens R. J. Tscheka, Stuttgart (DE); Nirna Keramati Noori, Toronto (CA)

(72) Inventors: Nariman Keramati Noori, Stuttgart (DE); Clemens R. J. Tscheka, Stuttgart (DE); Nirna Keramati Noori, Toronto (CA)

(*) Notice: Subject to any disclaimer, the term of this patent is extended or adjusted under 35 U.S.C. 154(b) by 834 days.

(21) Appl. No.: 17/255,674

(22) PCT Filed: Jun. 26, 2019

(86) PCT No.: PCT/IB2019/055403
§ 371 (c)(1),
(2) Date: Dec. 23, 2020

(87) PCT Pub. No.: WO2020/003159
PCT Pub. Date: Jan. 2, 2020

(65) Prior Publication Data
US 2021/0235758 A1    Aug. 5, 2021

Related U.S. Application Data

(60) Provisional application No. 62/689,999, filed on Jun. 26, 2018.

(51) Int. Cl.
*A24F 40/42*     (2020.01)
*A24F 40/20*     (2020.01)
*A24F 40/70*     (2020.01)

(52) U.S. Cl.
CPC .............. *A24F 40/42* (2020.01); *A24F 40/20* (2020.01); *A24F 40/70* (2020.01)

(58) Field of Classification Search
None
See application file for complete search history.

(56) References Cited

U.S. PATENT DOCUMENTS

| 4,989,619 A   * | 2/1991 | Clearman ................ A24D 1/18 |
| | | 131/194 |
| 2011/0186060 A1* | 8/2011 | Saleh ....................... A24D 1/14 |
| | | 131/173 |

(Continued)

*Primary Examiner* — Oscar C Jimenez
(74) *Attorney, Agent, or Firm* — RC Trademark Company

(57) ABSTRACT

A disposable capsule, containing herbal product such as cannabis, can be used with a vaporizer for vaporizing the volatile constituents. The limited battery capacity of portable vaporizers necessitates efficient energy use in order to generate vapor from the herbal product. This is achieved through various features of the invention. Aided by airtightness of the vaporizer capsule connection, the airflow through the capsule can be guided in a controlled fashion. In fact, the capsule (1) is for use in a vapor producing device, the capsule (1) being filled with a herbal product (30) and comprising a shell (202), an upstream part (40) and a downstream part (41), wherein an inlet orifice (401) is in the upstream part (40) and/or in the shell (202) and an outlet orifice (411) is in the downstream part (41), the inlet orifice (401) and the outlet orifice (411) comprising a multitude of perforations (10), and wherein a flow-through-area A2, being a combined surface area of the perforations (10) of the outlet orifice (411), is larger than a flow-through-area A1, being a combined surface area of the perforations (10) of the inlet orifice (401).

18 Claims, 19 Drawing Sheets

(56) References Cited

U.S. PATENT DOCUMENTS

| | | | | |
|---|---|---|---|---|
| 2014/0053832 A1* | 2/2014 | Postma | .................... | A24F 42/60 |
| | | | | 128/202.21 |
| 2014/0069446 A1* | 3/2014 | Haddad | ..................... | A24F 1/30 |
| | | | | 427/2.14 |
| 2015/0258288 A1* | 9/2015 | Sullivan | ................ | A24F 40/485 |
| | | | | 128/203.12 |
| 2016/0331913 A1* | 11/2016 | Bourque | ........... | A61M 15/0043 |
| 2019/0045833 A1* | 2/2019 | Saygili | ................. | A24B 15/167 |
| 2020/0268056 A1* | 8/2020 | Goldstein | ............... | A24F 42/60 |

\* cited by examiner

DISPOSABLE CAPSULE FOR THE EFFICIENT GENERATION OF HERBAL VAPOR WITH VAPOR PRODUCING DEVICES

BACKGROUND OF THE INVENTION

The present invention relates to the field of disposable capsules, cartridges or pods, containing herbal products intended for inhalation with vaporizers.

For centuries combustion of various substances, including tobacco and cannabis, and inhalation of the respective fumes has been utilized as an efficient and fast means of delivery to the body. Through inhalation of combustion fumes, high bioavailability and systemic presence of pharmacological constituents can be achieved. Over the years, extensive research and epidemiological data revealed the hazardous effects of this effective pulmonary delivery practice. The toxic effects of combustion are attributed to the high energy ingress in an uncontrolled manner, altering both the chemical nature of the matrix as well as the structure of the desired volatile constituents, generating a variety of carcinogenic and toxic substances, causing harm to the tissue in contact. Vaporization on the contrary, allows for a controlled and mild energy ingress and exposure to a chosen temperature which (in the range of 120-250° C.) largely reduces undesired chemical modification and more exclusive release of desired volatile constituents through vaporization and sublimation. At the chosen temperature solely the sufficiently volatile constituents of the herbal product will be vaporized and made available for inhalation without substantial thermal degradation, rendering this administration technique more effective.

The medical use of cannabis is broad and allows for therapeutic intervention for conditions such as anorexia and cachexia due to cancer and HIV/AIDS, glaucoma, nausea, pain, seizures, spasms, epilepsy, inflammatory and autoimmune diseases, such as multiple sclerosis and inflammatory bowel disease (IBD), among others. The therapeutic effect of cannabis is mainly attributed to the group of cannabinoids which act as agonists and activate the endocannabinoid system in the nervous and immune system. The endogenous transmitter acting on the cannabinoid receptors is not a single compound either, instead the agonists represent a group of lipid-based compounds produced by the body for this purpose. Administration of cannabinoids via inhalation allows for a pharmacological modulation of the endocannabinoids system which offers therapeutic intervention for said conditions to the desired extent.

Among vapor producing devices, portable devices, mainly using conduction as the heating concept, are gaining a bigger market share and have outranked stationary solutions. This can be attributed to higher convenience, flexibility and discretion. The portable devices usually don't consist of bulky components, such as vapor collection containers of stationary devices and are designed to be carried in a pocket in order to enhance the compliance to therapy of the user wherever it is needed. Most, but not all portable devices predominantly use the conductive heat transfer mechanism to transfer thermal energy to the herbal product, allowing for compact design of the device. This has implications on the geometry of the vapor producing device heating chamber; this cavity is usually narrower and deeper than for stationary devices. Convection is the other common heating mechanism, which is predominantly used for stationary solutions. Convection units employ heated air in order to collect volatile compounds from the herbal product. Nonetheless, the operating mechanism is not exclusive, both effects (conduction and convection) contribute to heating; the dominant mechanism dictates the assignment to the respective group.

In order to systematically utilize the therapeutic potential of vaporization for the various conditions described above, adequate dosing for each indication is essential. For this reason, the correct filling of the vapor producing device is crucial, which can be vastly improved through standardization with prefilled capsules. In terms of predictability, consistency and reliability the prepackaging of the herbal product in disposable capsules is superior towards manual filling of the vapor producing device for each use. The use of capsules reduces the need to meticulously maintain the vapor producing device in order to allow for consistent operation, because no sticky herbal residue can build up in the heating chamber of the vaporizer, deteriorating the heat transfer to the herbal product. Furthermore, stability towards degradation, contamination risk, microbiological safety and convenience of use are also improved. These benefits of disposable capsules filled in a standardized manner and administered with the respective vapor producing device have already been recognized. The prior art discloses ecosystems consisting of a device, system and method, including a single-use capsule for its proprietary vapor producing device. The basic design of these prior art capsules does not address the requirement for a portable device, necessitating an efficient utilization of the limited battery capacity of the vapor producing device. Neither, do these capsules, containers or pods exhibit features that enhance the value for portable vapor producing devices, as the disposable capsules disclosed herein. Nor does the prior art describe features permitting to design capsules for the majority of available vaporizers and the geometrical constraints of their heating chambers, in comparison to this disclosure.

The efficiency of the vaporization can be improved through control over the airflow through device and capsule. Leakage flow, diminishing efficiency, is prevented through the tightness of the capsule within the vaporizer. Minimizing heat transfer losses from the device to the capsule is another cornerstone for efficient vaporization. Through optimal surface contact and alignment of the capsule within the vaporizer, the thermal isolation by air can be reduced. The orifices with their perforations in the capsules can serve more purposes than granting access of the extraction air to the herbal product, which has not been addressed by the prior art. If the airflow through the capsule is optimized, vaporization at the given temperature can be significantly increased without further heat stress exerted on the herbal product, potentially causing the formation of toxicants known from combustion and unnecessarily further draining the battery. This optimization is achieved by restricting airflow into the capsule through specific design of the inlet orifice, reducing the atmospheric pressure during inhalation.

BRIEF SUMMARY OF THE INVENTION

The present invention is directed to a capsule for use in a vapor producing device, the capsule being filled with a herbal product and comprising a shell, an upstream part and a downstream part, wherein an inlet orifice is in the upstream part and/or in the shell and an outlet orifice is in the downstream part, the inlet orifice and the outlet orifice comprising a multitude of perforations and wherein a flow-through-area A2, being a combined surface area of the perforations of the outlet orifice, is larger than a flowthrough-area A1, being a combined surface area of the perforations of the inlet orifice. The invention is further directed to a vapor producing device, preferably a portable vapor producing device, comprising the capsule, and to a use of the capsule in a vapor producing device, comprising a heating chamber with sidewalls, wherein the capsule is inserted airtight into the vapor producing device and preferably the shell is pressed tightly to the sidewalls of the heating chamber.

At the inlet orifice and the outlet orifice, respectively, the flow or airflow passes through the multitude of perforations, also referred to as openings, into or out of the capsule. The flow-through-area A1 is understood to present the sum of the areas, through which the flow can pass at the inlet orifice into the capsule, and the flow-through-area A2 is understood to present the sum of the areas, through which the flow can pass the outlet orifice out of the capsule, respectively.

A disposable capsule, containing herbal product such as cannabis, can be used with a vaporizer for vaporizing the volatile constituents. The limited battery capacity of portable vaporizers necessitates efficient energy use in order to generate vapor from the herbal product. This is achieved through various features of the invention. Aided by airtightness of the vaporizer capsule connection, the airflow through the capsule can be guided in a controlled fashion. The specific layout of the orifices of the capsule impacts the airflow through the capsule, giving rise to enhanced vaporization through pressure reduction within the capsule without additional energy ingress, draining the battery. Heat transfer through conduction can be enhanced through tightly pressed capsules within the vaporizer, minimizing the isolating effect of air. Design features of the capsule permit to engineer capsules for the majority of currently available vaporizers and the respective geometrical requirements.

The present invention is a disposable capsule which is filled with herbal product whereas the filled capsules are intended to be inserted into a vapor producing device, which includes portable vaporizers, in order to generate vapor for inhalation. The capsule comprises or consists of a shell as well as an upstream and a downstream part.

The optimization of the airflow through the capsules enhances the efficiency of vaporization, which is particularly relevant for portable devices with limited battery capacity. We disclose concepts to prevent leakage flow between the capsule and the device in order to maximize the airflow through the capsule in a controlled manner. If guided in a controlled fashion through the capsule, the air can serve more purposes than as an extraction means for volatile substances as in the prior art. Restricting the flow of the air through the inlet orifice gives rise to an atmospheric pressure drop, which decreases the boiling temperature of the volatile constituents. The position and geometry of the inlet orifice in the upstream part or in the shell allow for the optimization of the airflow with respect to the heat energy required for the vaporization of the volatile compounds of the herbal product. Furthermore, the efficacy of heat transfer to the herbal product for heating predominately by conduction can be improved through concepts to tightly press the capsule to the heating chamber of the vapor producing device, preventing air to deteriorate heat transfer from the walls of the heating chamber, since heat conductivity of air is poor. In addition to these concepts to enhance efficacy, we disclose approaches that allow to engineer capsules for most currently available vaporizers considering the geometry of their heating chambers, which has not been reported in prior art.

BRIEF DESCRIPTION OF THE DRAWINGS

The features believed to be characteristic of the capsule according to this disclosure, as to their organization, structure, use, and method of operation, together with further advantages and objectives thereof, will be better understood from the subsequent illustrations in which an embodiment of the disclosure will be depicted by way of example. It is expressly noted that the figures are for the purpose of description and illustration only, and are not intended as a definition of the limits of the invention.

DETAILED DESCRIPTION AND BEST MODE OF IMPLEMENTATION

Figure 1:
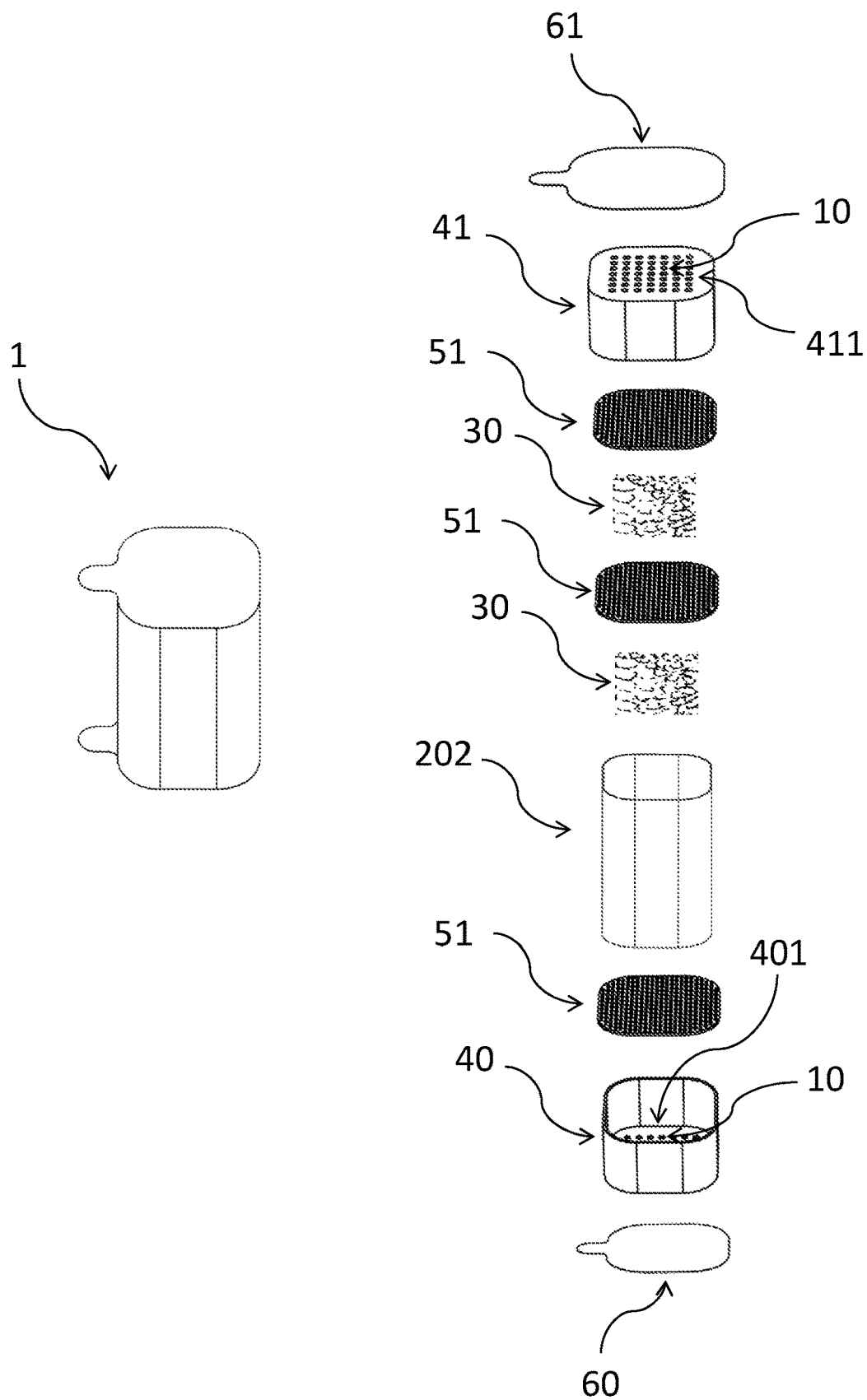
FIG. 1 shows an exploded perspective view of the capsule (1) for holding a herbal composition (30) on the right side and an isometric view of the assembled capsule (1) on the left side, in accordance with an embodiment.

The following description is provided to enable any person skilled in the art to practice the various aspects described herein. Various modifications, alterations, and improvements to these aspects will be readily apparent to those skilled in the art, and the generic principals defined herein may be applied to other aspects. These modifications, alterations, and improvements are intended to be part of this disclosure and are intended to be within the spirit and scope of the invention. Accordingly, the foregoing descriptions and drawings are by way of example only. Unless context clearly dictates otherwise, the meaning of "a", "an" and "the" also includes plural references.

The illustrations are not necessarily to scale and in some instances proportions may have been exaggerated in order to describe the respective feature and embodiment more clearly.

As used herein, a person skilled in the relevant art may generally understand the term "comprising" to generally mean the presence of the stated feature, integers, steps, or components as referred to in the claims section, but that it does not preclude the presence or addition of one or more other features, integers, steps, components or groups thereof.

The invention presented herein is applicable to various herbal products for various applications including therapeutic and medical use among others.

The various herbal products include cannabis (such as the cannabis strains *Cannabis sativa, Cannabis indica, Cannabis ruderalis*) or marijuana, containing cannabinoids, such as Cannabidiol (CBD), Cannabigerol (CBG), Cannabinol (CBN), Tetrahydrocannabinol (THC), Tetrahydrocannabivarin (THCV) in various ratios, among others, but are not restricted to the mentioned examples. The herbal product may include cannabis as mentioned above, tobacco, spices, tea (chamomile, gingko, mango, mint, etc.), leafy food products and other loose-leaf sources as well as herbal extracts, distillates, concentrates (such as cannabinoid waxes and oils) and derivatives of the sources mentioned before and combinations thereof. The herbal product may also contain compounds from the groups of amino acids, enzymes, esters, fatty acids, flavonoids, proteins, terpenoids and other compounds and combinations thereof. Additives to the herbal products are not restricted to dry particulate materials. These additives include substances in any physical state, such as solids, semi-solids and liquids as well as combinations thereof. The blend may exhibit desirable properties which the single compounds do not provide. Tailoring the ratio and content of active constituents such as THC and CBD through addition of single constituents or blending may increase the quality of the treatment for the respective purpose. Addition or blending may be required for technical reasons such as the filling process.

To vaporize or vaporization in the sense of the invention is the generation of vapor. Vapor represents inhalable matter, containing the active or desired compounds from the herbal product. The vapor may include inhalable matter in any physical state, including aerosols consisting of solid and/or liquid compounds and/or particles (mist), which are suspended in air, and/or gaseous compounds. Over the course of the inhalation process, the physical state can change, for example through cooling down. Particles of any physical state can reach the lungs, depending on their aerodynamic properties, mainly the particle size. The physicochemical state of the vapor includes lipophilic (e.g. oil, wax), hydrophilic compounds or phases (e.g. water, watery extracts) and mixtures thereof suspended in air, and/or gaseous compounds.

A vapor producing device in the sense of the invention is an apparatus with which vapor can be generated. Vapor producing devices include various variants of vaporizers, including portable, handheld, stationary, with and without a collection container for the vapor, among others.

Consequently, vapor in the sense of this invention is vapor, generated from the herbal product with a vapor producing device, as both described above. The vapor is administered through inhalation.

A disposable capsule in the sense of the invention means, that the entire capsule or a part of the capsule is discarded after consumption of the herbal product. The disposable capsule is not intended to be refilled manually by the user.

For administration of the herbal product to the user, the capsule is inserted into the vapor producing device. Synonyms for capsule are pod and cartridge.

An embodiment of the capsule (1) and its components is illustrated in FIG. 1. The capsule (1) comprises a shell (202) in conjunction with an upstream (40) and a downstream part (41), preferably the capsule (1) consists of a shell (202) in conjunction with an upstream (40) and a downstream part (41), which separates an internal volume from the surroundings. These components can also carry the perforations (10) of the inlet orifice (401, FIG. 1, FIG. 7) and outlet orifice (411, FIG. 1, FIG. 7). The internal volume may be divided into compartments through membranes (51) or separators (207i, FIG. 2). The capsule (1) may contain membranes (51), helping to keep the herbal product (30) in place, ensuring a consistent flow and flow resistance, as well as permitting homogenous heat transfer to the entire herbal product (30). The capsule (1) can also carry seals (60, 61), namely an upstream (60) and/or a downstream seal (61), in order to seal the inlet (401, FIG. 1, FIG. 7) and outlet orifices (411, FIG. 1, FIG. 7) from the surroundings and preserve the herbal product (30) during transportation and storage until the time of use.

Figure 2:
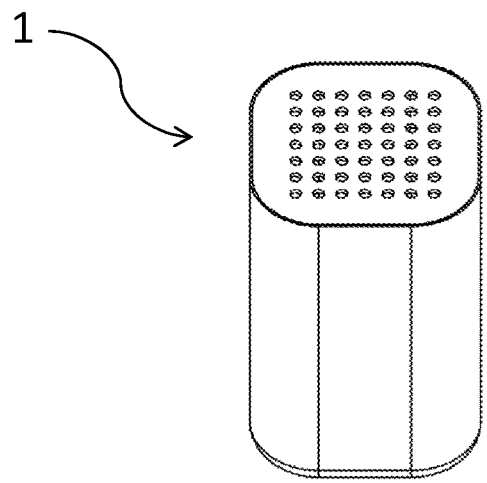
FIG. 2 shows a capsule (1) and illustrates different views of the shell, showing two concepts of the shell (202), one with a separator part (207i) inside the shell (202) and the other one without, each in accordance with an embodiment.
Figure 2:
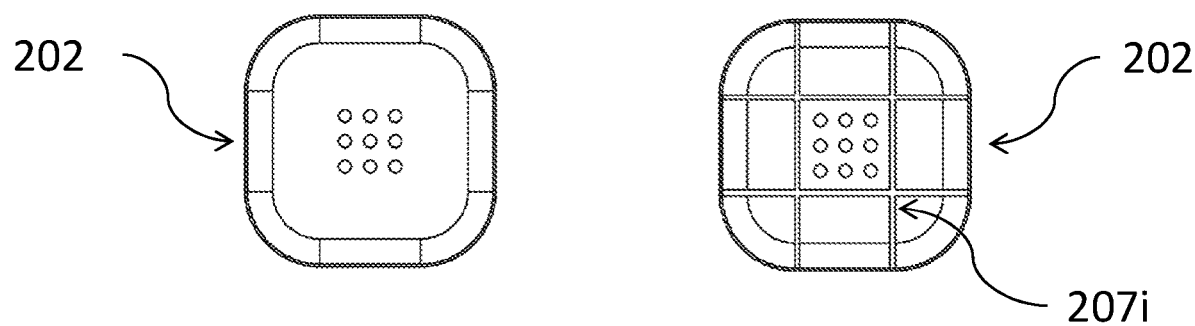
Figure 2:
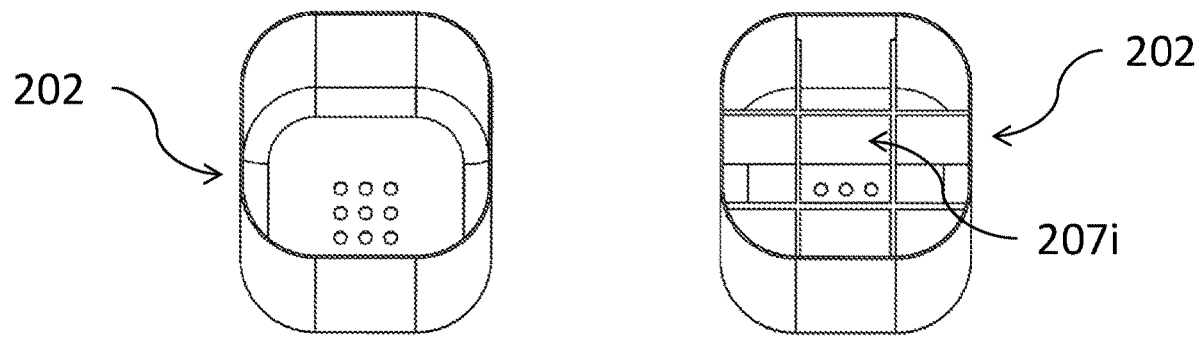

The capsule (1) may carry separators (207i, FIG. 2). The separators (207i) can be a part of the shell (202, FIG. 2) or be a separate part. The capsule (1) may comprise a separator (207i) or separators (207i) that are preferably part of the shell and/or the capsule (1) may comprise a separator (207i) or separators (207i) being separate. An embodiment of the shell (202) without separators (207i) and an embodiment of the shell (202) with separators (207i) are shown in FIG. 2. The separator (207i) improves the structural integrity of the capsule (1) and also leads to homogenous heat transfer to the herbal product (30, FIG. 1). Furthermore, the separator (207i) can be used to separate different types of herbal products (30) and helps to retain the respective herbal product (30) in position for example during transportation and use of the capsule (1).

The shell and/or the upstream and/or the downstream part preferably consist of a material, which is impermeable for fluids, namely gas and/or liquids, especially air and/or vapor. Preferably, the shell, the upstream part and/or the downstream part consist of an impermeable and/or deformable material. The shell and/or the upstream and/or the downstream part may comprise or consist of any suitable material, such as medical or food grade materials, that is deformable, including aluminum, aluminum alloys, stainless-steel alloys, titanium, titanium alloys, copper, copper alloys, plastics, high-performance plastics, paper, hemp and compressed herbal product and combinations thereof. Preferably, the shell and/or the upstream and/or the downstream part consist of aluminum, aluminum alloys, stainless-steel alloys, titanium, titanium alloys, copper, copper alloys, plastics, high-performance plastics, paper, hemp and compressed herbal product and combinations thereof. The membranes and/or the separators may comprise or consist of any suitable material, such as medical or food grade materials, including aluminum, aluminum alloys, stainless-steel alloys, such as stainless-steel screen mesh filters, titanium, titanium alloys, copper, copper alloys, plastics, high-performance plastics, fabric, fleece, other fibrous arrangements and combinations thereof. Preferably, the membranes and/or the separators may consist of aluminum, aluminum alloys, stainless-steel alloys, such as stainless-steel screen mesh filters, titanium, titanium alloys, copper, copper alloys, plastics, high-performance plastics, fabric, fleece, other fibrous arrangements and combinations thereof.

Figure 3:
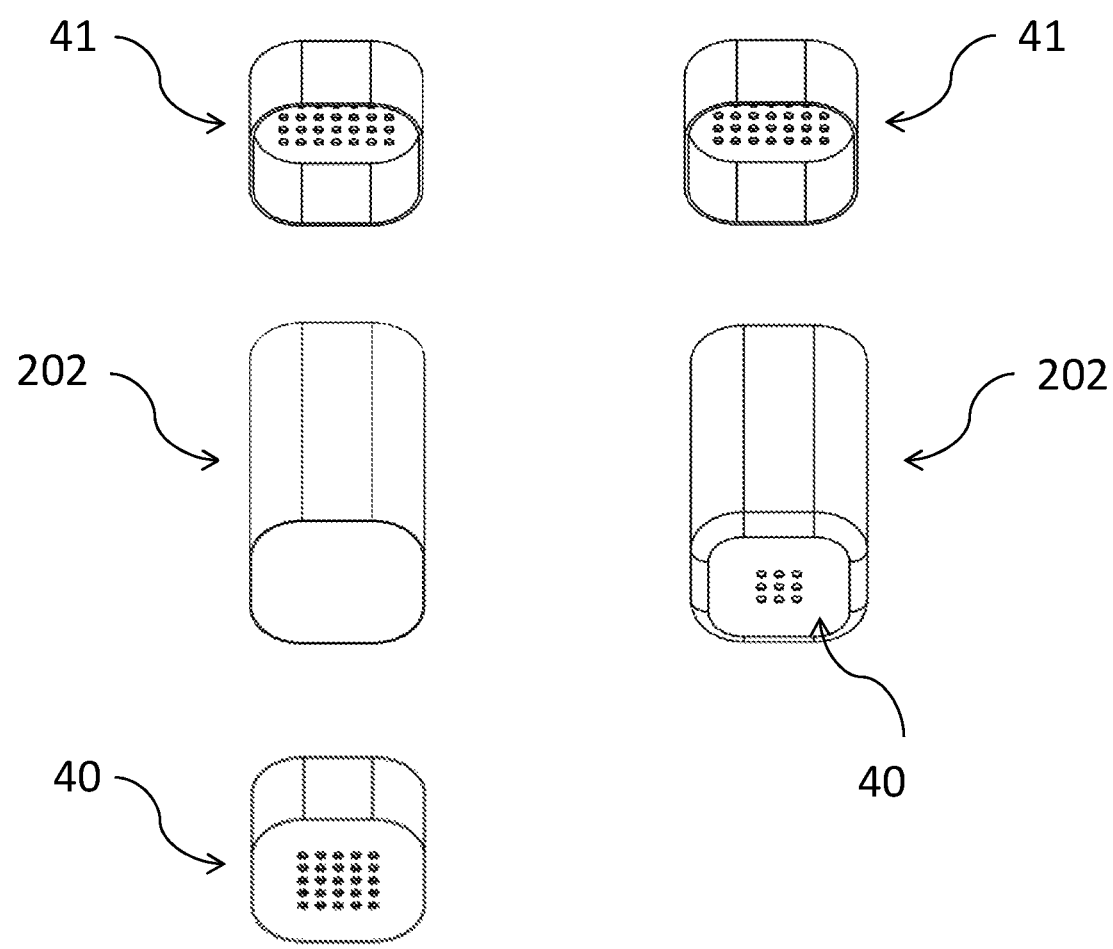
FIG. 3 presents an exploded isometric view of two different concepts of the capsule, showing the upstream part (40) as a separate part or as a part of the shell (202), each in accordance with an embodiment.

The upstream (40) and/or downstream part (41) may be part of the shell (202). The upstream (40) and/or downstream part (41) may be separate parts, which can be permanently or removably connected to the shell (202), allowing straightforward filling of the capsules during production. Additionally, the removable connection may provide access to the herbal product (30, FIG. 1) for the user. The upstream part (40) can also be a part of the shell (202). Two of these variants are illustrated in FIG. 3, each in accordance with an embodiment.

Figure 4:
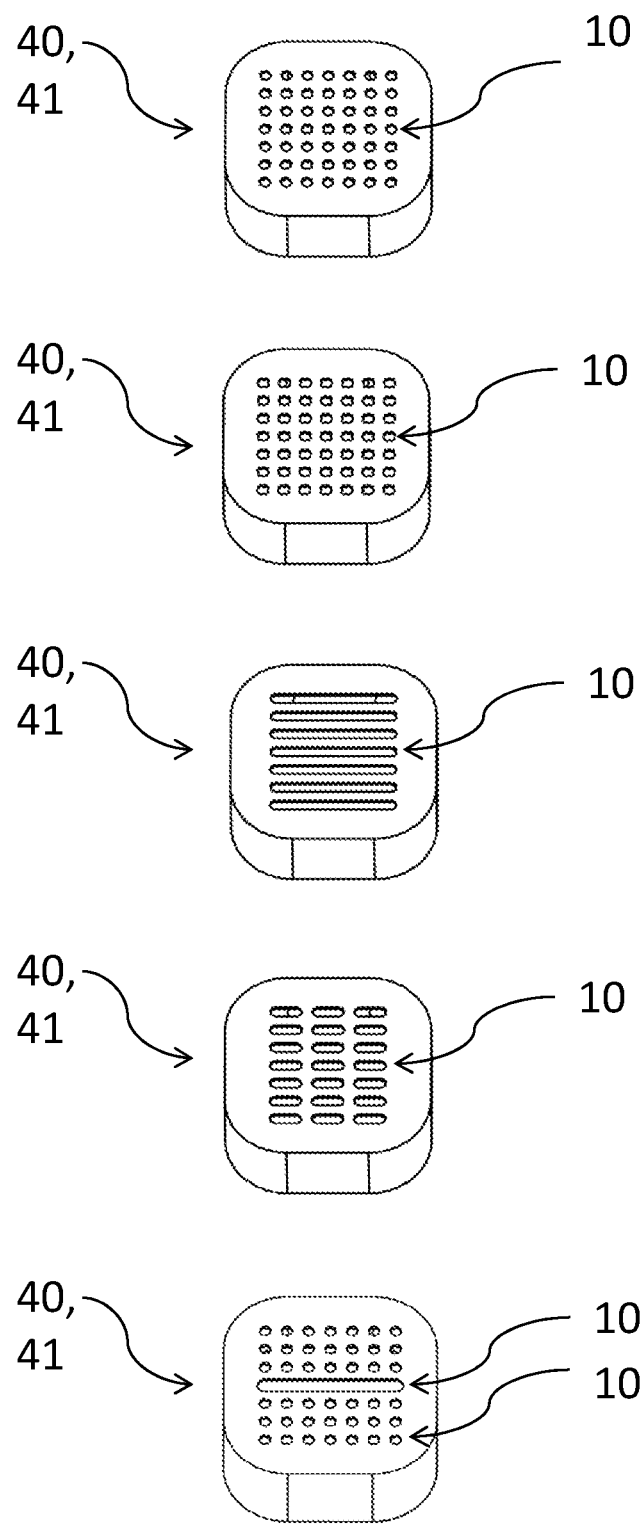
FIG. 4 depicts isometric views of five different forms of the upstream (40) or downstream part (41) showing different perforation (10) styles, $1^{st}$ from the top exhibits circular perforations (10), $2^{nd}$ from the top exhibits rectangular perforations with rounded vertices (10), $3^{rd}$ from the top exhibits slit-shaped perforations (10), $4^{th}$ from the top exhibits elongated perforations (10) and the $5^{th}$ from the top combines a multitude of circular perforations (10) and a slit-shaped perforation (10), each in accordance with an embodiment.

The upstream (40, FIG. 3) and/or downstream parts (41) and/or the shell (202) may exhibit perforations (10, FIG. 4). In embodiments presented in FIG. 4, the geometries and shapes of the perforations (10) may be circular, rectangular, rectangular with rounded vertices, slit-shaped and elongated shapes, all other suitable shapes as well as combinations thereof, such as the combination of a multitude of circular perforations (10) and a slit-shaped perforation (10). The shape of the perforations (10) can differ between the shell (202, FIG. 3), upstream (40) and the downstream part (41). A perforation (10) is any opening in the capsule (1, FIG. 1) through which (air)flow either enters or exits the capsule (1). The perforations allow for the permeation of extraction air through the capsule (1, FIG. 1) on one hand and reduce airborne particles from the herbal product (30, FIG. 1) through the extraction air on the other hand. Airborne particles may clog the vapor producing device or may cause an irritating sensation for the user during inhalation.

Figure 5:
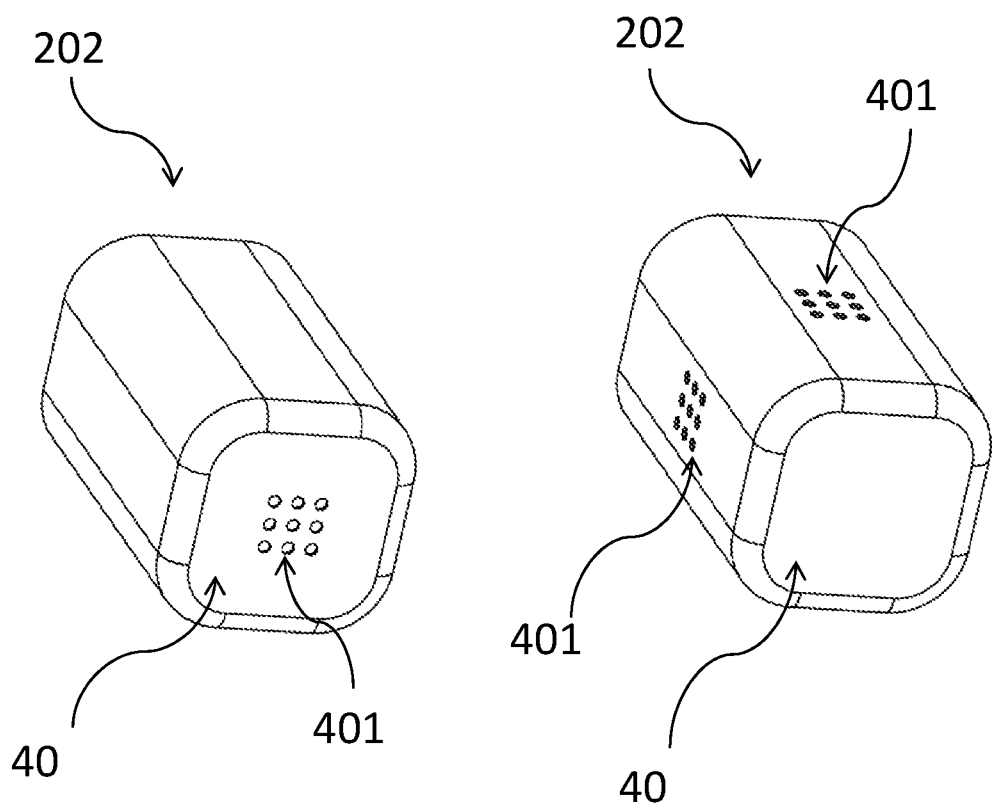
FIG. 5 presents an isometric view of two concepts of the shell with the upstream part (40) which is part of the shell (202), showing variants of different inlet orifice (401) positioning, on the left the inlet orifice (401) is positioned in the upstream part (40), on the right the inlet orifice (401) is positioned in the shell (202), each in accordance with an embodiment.

Depending on requirements for the airflow and geometrical constraints given by the design of the vapor producing device, the positioning of the perforations of the inlet orifice can vary. FIG. 5 depicts two concepts of the shell (202), each in accordance with an embodiment. In one concept, in which the upstream part (40) is a part of the shell (202), the inlet orifice (401) is placed on the upstream part (40). In another concept, the inlet orifice (401) is positioned on the shell (202) and the upstream part (40) is without perforations (10, FIG. 4).

Figure 6:
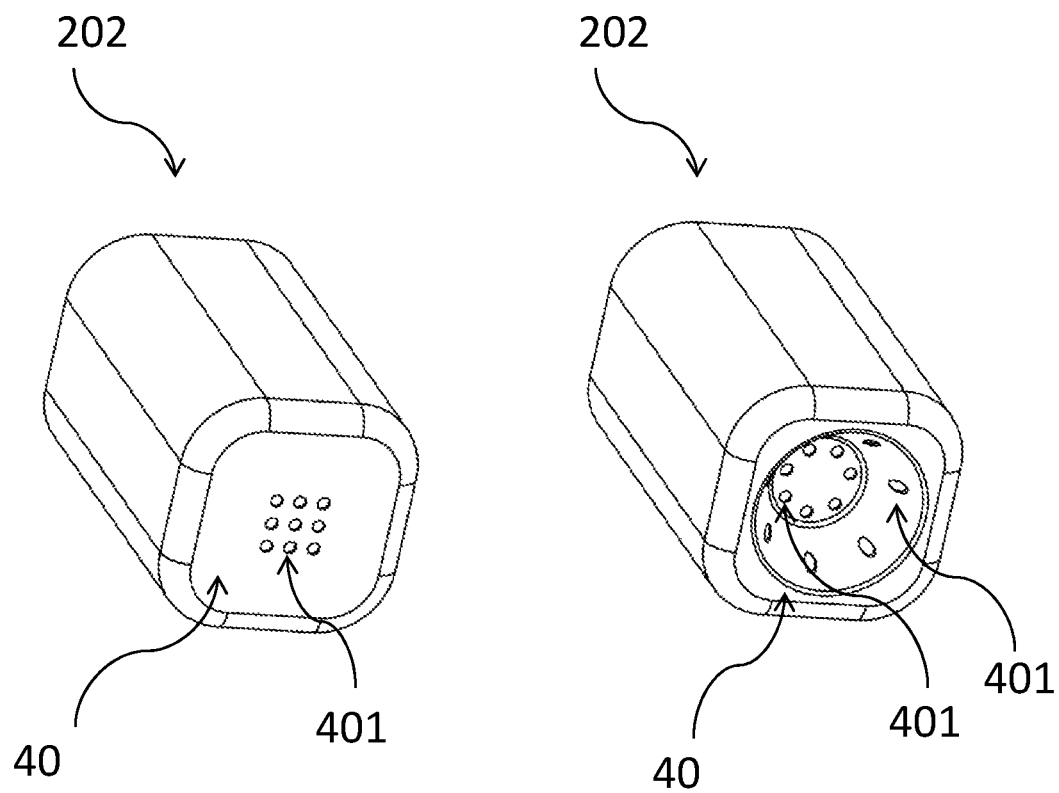
FIG. 6 presents an isometric view of two concepts of the shell, showing variants of the upstream part (40) shape as a part of the shell (202), on the left the upstream part (40) shape is flat, on the right the upstream part (40) has an inward raised shape, each in accordance with an embodiment.

Likewise, the shape of the upstream (40, FIG. 1) and downstream part (41, FIG. 1) can also vary depending on the type of the vapor production device (conduction, convection or mixture of the two) and due to geometrical constraints. In FIG. 6 two concepts of the shell (202) are shown, in which the upstream part (40) is a part of the shell (202), each in accordance with an embodiment. The shape of the upstream part (40) can be flat, have an inward raised shape, an outward raised shape or be any in-between transition shapes thereof. The upstream part (40) can carry perforations (10, FIG. 4) of the inlet orifice (401).

Figure 7:
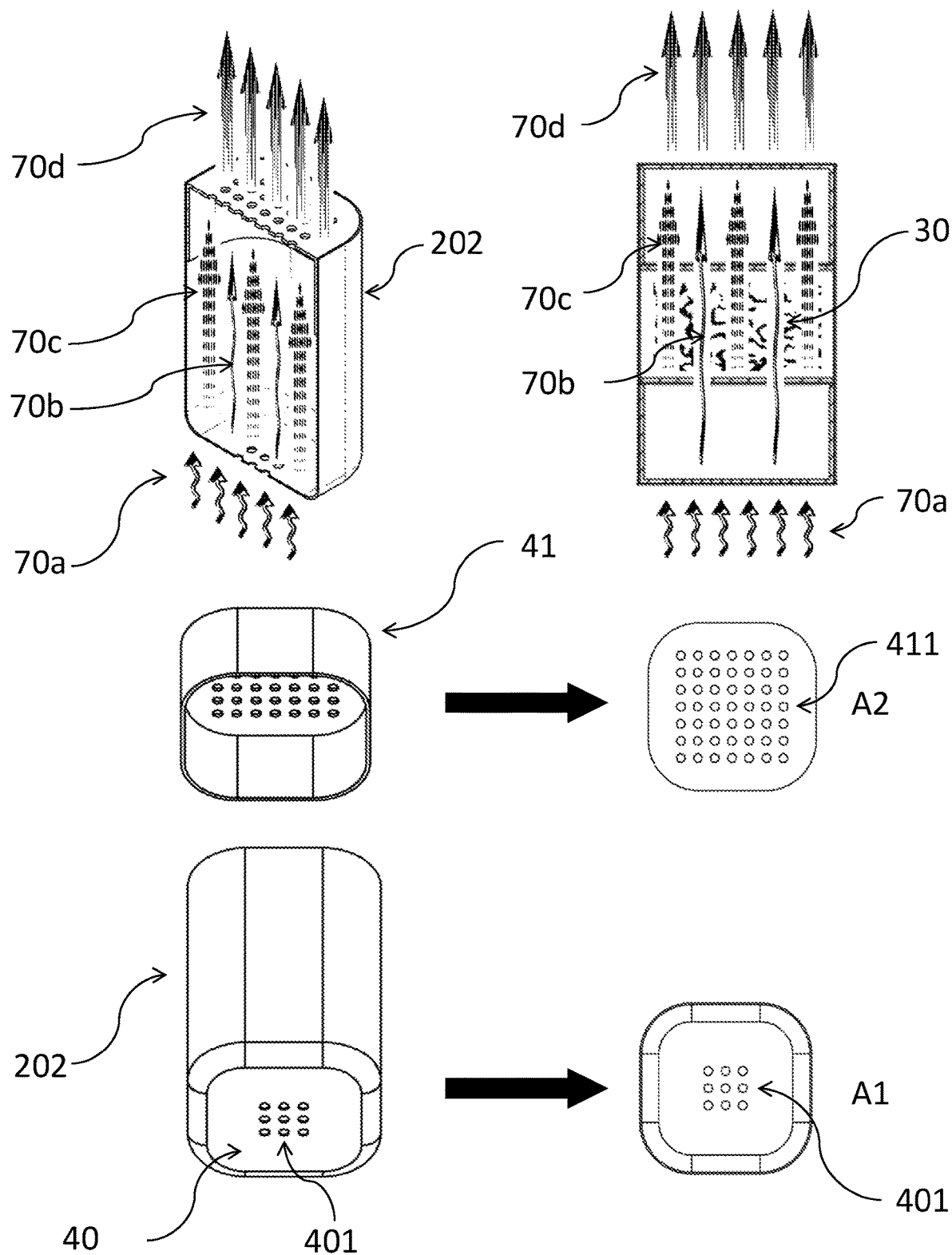
FIG. 7 shows different views of the capsule depicting the effect of the atmospheric pressure reduction during inhalation which is created through diminished inlet flow-through-area A1 in comparison to the outlet flow-through-area A2, in accordance with an embodiment.

The configuration of the perforations influences the airflow through the capsule; the amount, size, shape, distribution and position are particularly relevant here. The inlet orifice is the combination of any perforation or any other opening in the capsule through which (air)flow enters the capsule during the inhalation process. The outlet orifice is the combination of any perforation or any other opening in the capsule through which (air)flow exits the capsule during the inhalation process. Both the inlet and the outlet orifice of the capsule can comprise or consist of a multitude of perforations. The inlet orifice can be in the upstream part and/or in the shell of the capsule; the outlet orifice can be in the downstream part. Optimization of the airflow through the perforations of the inlet and the outlet orifice and their respective flow resistance allows for a (atmospheric) pressure reduction in the capsule, which increases evaporation of the desired volatile substances. Atmospheric pressure in this context is the pressure exerted by surrounding air within the atmosphere. Synonyms for atmospheric pressure are air pressure and barometric pressure. The effect of reduced atmospheric pressure on evaporation is known from high altitude climbing and is a general phenomenon for which only a few exemptions exist. The lower atmospheric pressure reduces the boiling point (as well as the sublimation temperature) at higher altitudes. In order to harness this phenomenon for the capsule design, the flow, passing through the vapor producing device at the inlet orifice (401, FIG. 7) of the capsule (1, FIG. 1), is restricted. The flow resistance of the operational device, carrying the capsule (1), is dictated by the flow resistance of the inlet orifice (401). An embodiment of this feature of the capsule (1) is illustrated in FIG. 7. More specifically, FIG. 7 depicts the airflow upstream of the capsule (70*a*), airflow after having passed the inlet orifice (401) or airflow inside the capsule (70*b*), generated vapor inside the capsule (70*c*) and a mixture (70*d*) of both the generated vapor and the airflow downstream of the capsule outlet orifice (411). Throughout the air pathway, the inlet orifice of the capsule (401) exhibits the lowest flow-through-area A1, in this example being placed in the upstream part (40), which is part of the shell (202). A1 is the combined surface area of the perforations (10, FIG. 4) of the inlet orifice (401) and A2 is the combined surface area of the perforations (10, FIG. 4) of the outlet orifice (411). The flow resistance of the downstream part (41) is lower, causing the atmospheric pressure drop through the inhalation process in the air pathway downstream of the inlet orifice (401), which includes the capsule volume. The capsule volume is the internal volume of the capsule (1). The lower flow resistance of the downstream part (41) is achieved because the flow-through-area A2 is larger than the flow-through-area A1. Preferably, a ratio between the flow-through-area A2 and the flow-through-area A1 is from 1.5:1 to 15:1, especially from 1.5:1 to 12:1, or especially from 3:1 to 15:1, or especially from 3:1 to 12:1, or especially from 5:1 to 15:1, more preferably from 5:1 to 12:1. Consequently, less energy is required from the battery of the vapor producing device in order to reach the temperature at which vaporization takes place and the thermal degradation and stress on the herbal product (30) is reduced as well. Additionally, vaporization increasingly occurs during inhalation, because of the auxiliary effect of the pressure reduction, meaning that less volatile constituents are dissipated unemployed.

The perforation diameter in the upstream part, downstream part and/or the shell, as well as the (average) pore size of the optional membranes, may be at least 10% smaller than the average particle size of the herbal product or may exhibit any suitable size. For elongated shapes, the feature size with the least extension is to be considered.

The surface area of the herbal product impacts its degradation, the speed and extent of extraction through air during use and consequently the pharmacokinetics and effect of the volatile agents. Furthermore, the particle size affects the flow characteristics for filling, the demixing tendency and the tendency to clog perforations. Likewise, particle size homogeneity is another crucial parameter for extraction, filling and demixing. For reproducible vapor generation, which allows more precise and accurate dosing, the filling of the capsules is crucial. Demixing during filling and transportation must be avoided. This can be achieved through compression of the filling material, ensuring monodisperse particle size of the filling material, or use of support membranes or separators, which prevent inhomogeneous redistribution of the filling material. Excipients may be used for the filling process.

Figure 8:
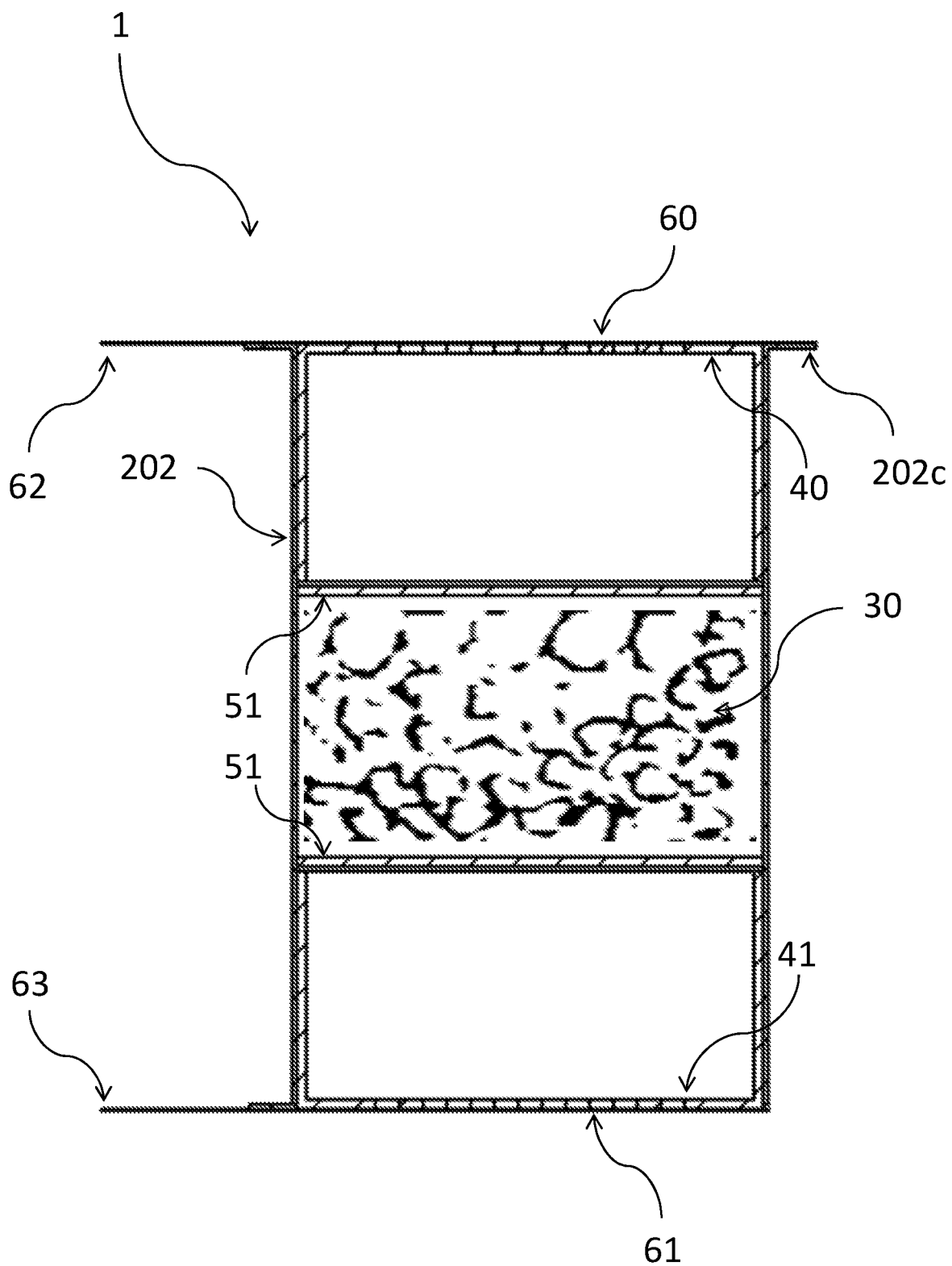
FIG. 8 illustrates a cross-sectional front view of the assembled capsule (1) in accordance with an embodiment.

In an embodiment of the capsule (1, FIG. 1), the upstream (40) and/or downstream part (41) may carry a seal (60, 61), namely an upstream (60) and/or a downstream seal (61), that seals the capsule (1) and is releasably connected; this is presented with a cross-sectional view of capsule (1) in FIG. 8. The capsule (1) may have a flange (202*c*), for example a flange (202*c*) on the upstream part, which is covered by a seal (60). The seal (60, 61), especially the upstream seal (60) and/or the downstream seal (61), may carry a flap (62, 63), especially an upstream flap (62) and/or a downstream flap (63), respectively, in order to facilitate the lift-off. Each of the seals (60, 61) may be removed before application or pinched automatically or manually. Alternatively, the seal may cover larger fractions of the shell (202), or the entire capsule (1), or several capsule units (1) at once. The seal (60,61), namely the upstream seal (60) and/or the downstream seal (61), may comprise suitable materials including plastics (foil), metal (e.g. aluminum foil), composites and combinations thereof, preferably the seal (60, 61) may consist of suitable materials including, plastics (foil), metal (e.g. aluminum foil), composites and combinations thereof. Sealing may be performed through an appropriate method, such as vacuum sealing. The seal (60, 61) in conjunction with the external packaging protects the herbal product (30), which can be held in place by membranes (51). The loss of content of desired constituents through degradation can be vastly reduced, including microbiological degradation, for example through mold growth, degradation through light, humidity and oxidation. The seal (60, 61) prevents contamination, also including microbiological contamination, for example through mold growth. The ideal humidity can be preserved within the capsule (1) through the seal (60, 61). Moisture content differs for processes such as curing and/or decarboxylation. Decarboxylation in this context is the chemical conversion of Tetrahydrocannabinol acid (THCA) into THC, which occurs spontaneously to a limited extent during storage and more intensely during heating (vaporization, combustion, heating during baking, etc.); THC is regarded as the pharmacologically active form. Due to the protection of the herbal product (30), the shelf life can be increased. The seal (60, 61) can therefore serve to set conditions for ripening within the capsule (1). Oxygen may be purged by an inert gas or removed by vacuum treatment for the sealing process.

Figure 9:
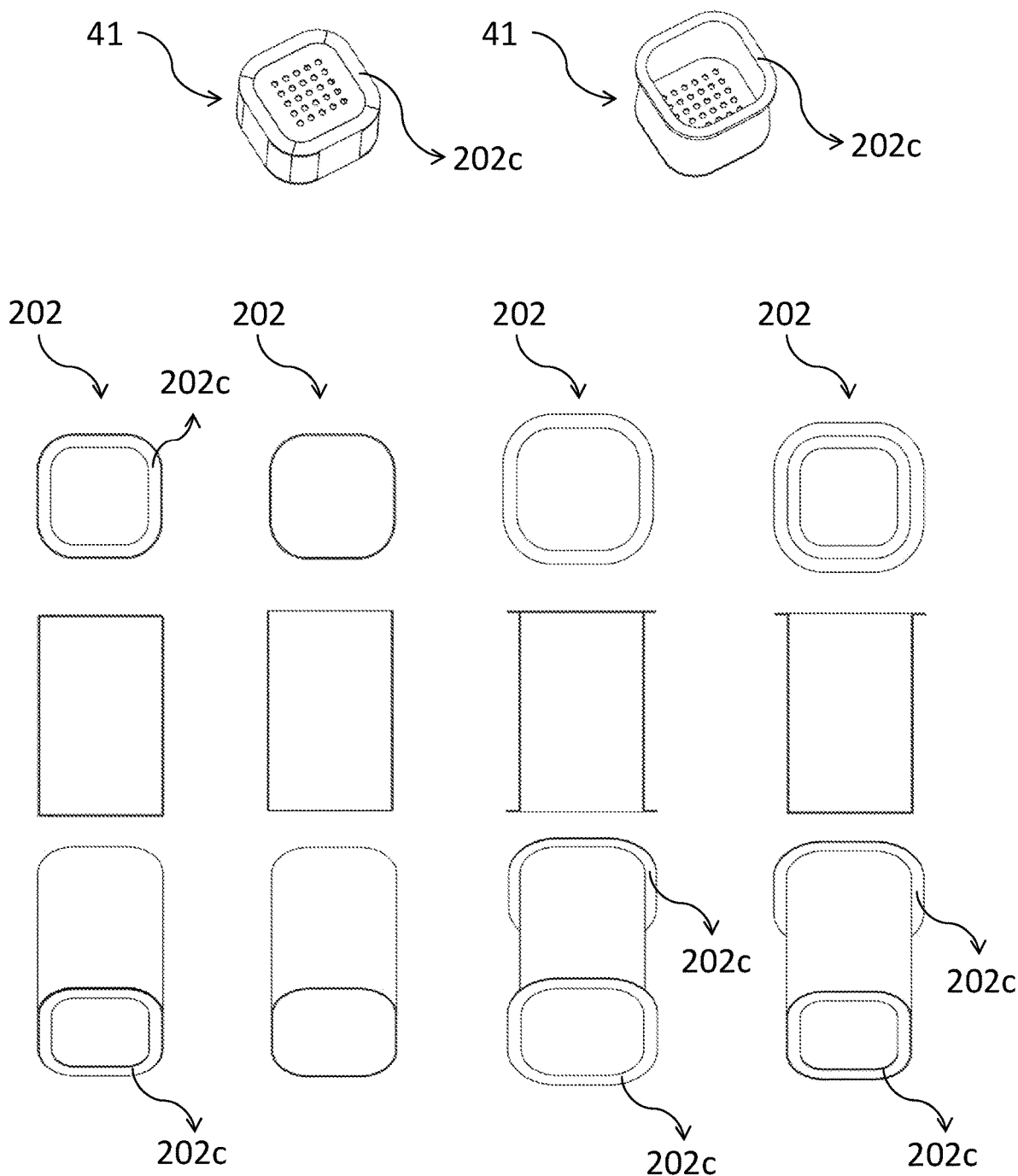
FIG. 9 depicts different views of the shell (202) (top view in $2^{rd}$ row, front view in $3^{rd}$ row and isometric view in $4^{th}$ row) and downstream part (41) (isometric view in $1^{st}$ row), showing variants of the capsule flange (202c) configuration, on the top left a foldable downstream part (41) with flange (202c) is displayed, on the top right an elongated downstream part (41) with flange (202c) is displayed, the $1^{st}$ flange configuration from the left shows flanges (202c) on the top and bottom of the shell (202) extending inwards, the $2^{nd}$ configuration from the left does not exhibit flanges, the $3^{rd}$ flange configuration from the left shows flanges (202c) on the top and bottom of the shell (202) extending outwards, the $4^{th}$ flange configuration from the left shows a flange (202c) at the top of the shell (202) extending outwards and a flange (202c) on the bottom of the shell (202) extending inwards, each in accordance with an embodiment.

The capsule (1, FIG. 1) may carry flanges (202*c*, FIG. 9) on which seals (60, 61, FIG. 1) can be attached. The positioning of the flanges (202*c*) can vary in order to account for the specific requirements, shape and size of the respective vapor production device. Shown in FIG. 9 are concepts differing in the position of the flange (202*c*), each in accordance with an embodiment. In some embodiments of the capsule (1), the flanges (202*c*) can be a part of the shell (202). In one configuration the flange (202*c*) may be situated on the top and bottom of the shell (202) extending inwards; in another configuration the flange (202*c*) extends outwards on the top of the shell (202) and inwards on the bottom of the shell (202), or in another configuration extends outwards both on the top and bottom of the shell (202), or the flange (202*c*) may either only be present in the top or the bottom of the shell (202) or any combination thereof. In some other embodiments of the capsule (1), the flanges (202*c*) can be a part of the upstream (40, FIG. 1) and/or downstream part (41), for example on an elongated (41, FIG. 14) or foldable downstream part (41, FIG. 13). In some embodiments of the capsule (1, FIG. 1), the shell (202) can be flangeless.

Figure 10:
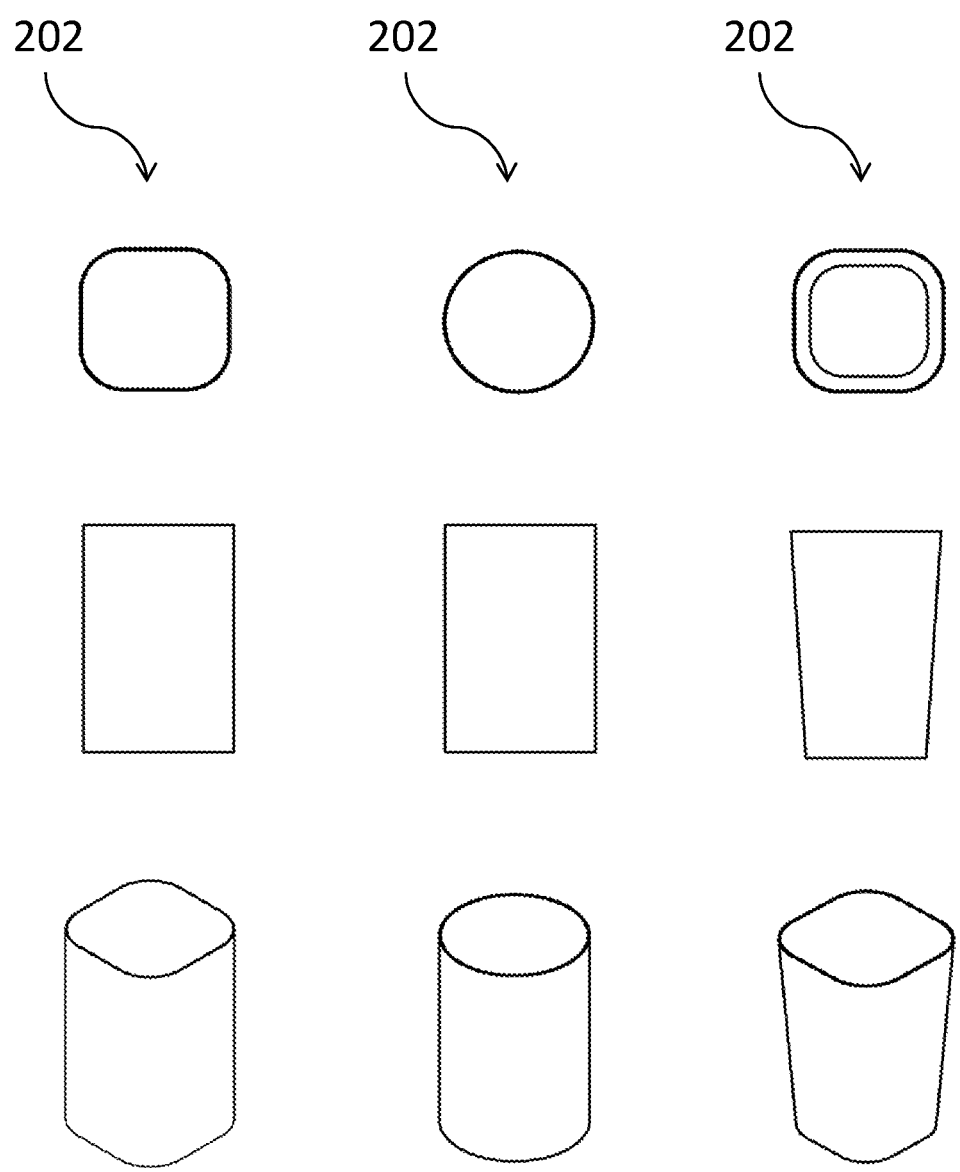
FIG. 10 illustrates top ($1^{rd}$ row), front ($2^{rd}$ row) and isometric ($3^{rd}$ row) views of three different shapes of the shell (202), the left shape is in form of a cube with rounded vertices, the shape in the center is cylindrical, more specifically the left and central shapes exhibit parallel walls in contrast to the shape on the right exhibiting draft angles to form a conical shape, each in accordance with an embodiment.

The design of the capsule differs depending on the geometry of the heating chamber (81, FIG. 15) of the vapor producing device. Different shapes of the shell (202) are presented in FIG. 10, each in accordance with an embodiment. In some embodiments of the capsule (1, FIG. 1), the shell (202) can be in form of a cube, a cube with rounded vertices, tubular, cylindrical, elliptical or any other similar shapes or any transition shapes of those shapes among other shapes. In some embodiments of the shell (202), the sidewalls can be fully vertical if the capsule stands upright, meaning that the sidewalls are parallel, furthermore the sidewalls can have draft angles to form conical and tapered shapes as well as having convex or concave shapes or any combinations thereof. The shapes of the shell (202) may also be non-symmetrical. Preferably, the shell (202) has a conical or convex shape.

Figure 11:
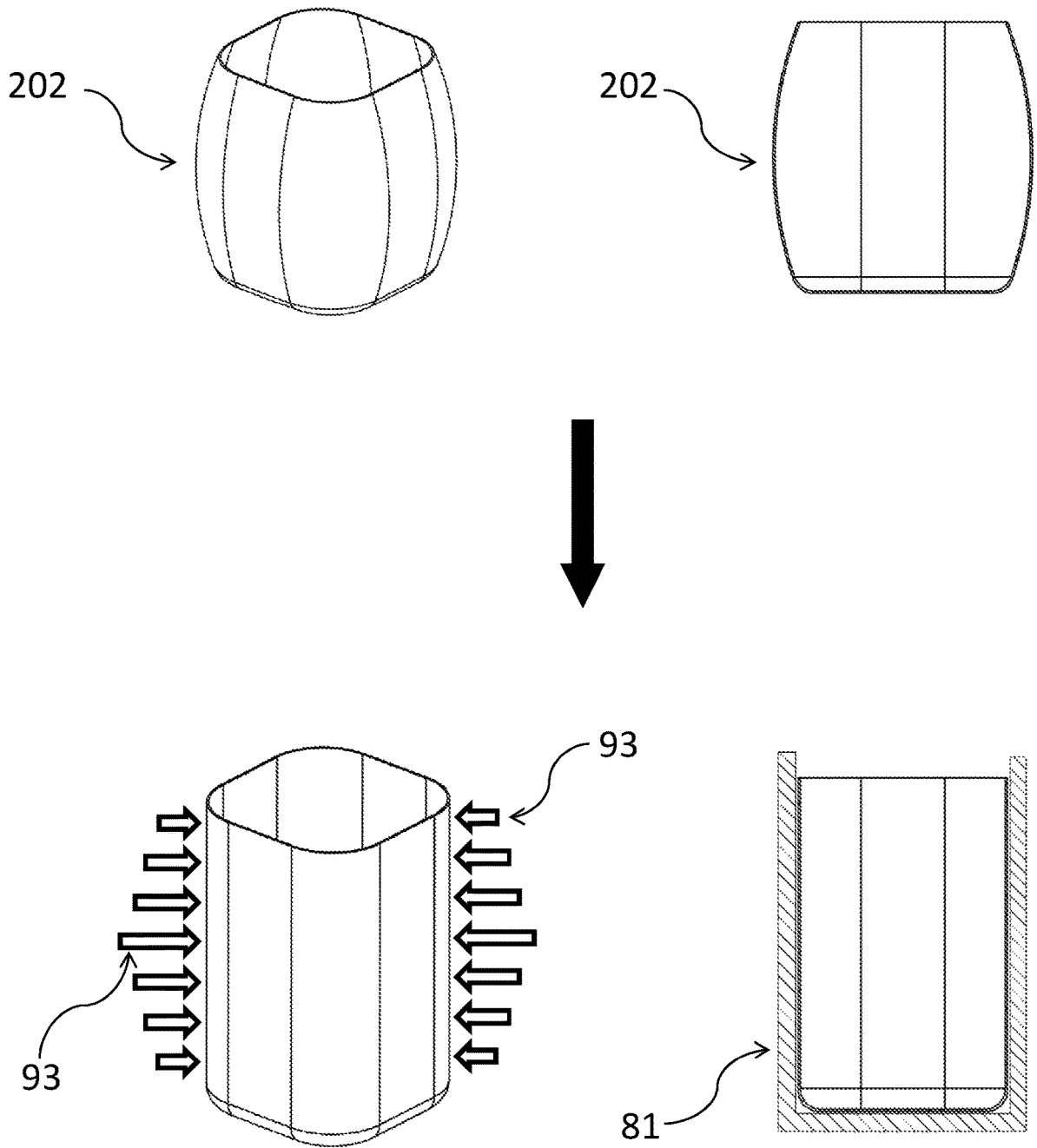
FIG. 11 illustrates the press-fit concept with isometric (left) and cross-sectional (right) views, in accordance with an embodiment.

Maximum heat transfer is of particular importance for portable vapor producing devices because of the lower battery drain of the limited battery capacity. Furthermore, the lag time for heating until the operating temperature is reached can be decreased, which is more convenient. For an effective heat transfer from the heating chamber of the vapor producing device to the capsule, containing the herbal product, a press-fit of the capsule shell in the heating chamber with maximum contact area towards the walls of the heating chamber, behind which the heating coils are located, is essential. This is the general configuration of the heating elements for conduction vaporizers, representing the most popular class among portable vaporizers. A loose fit on the contrary, diminishes the efficacy of the heat transfer due to lower contact area between the capsule and the heating chamber and the isolating effect of air in areas without contact. The press-fit with high contact area can be achieved through the use of deformable shell material of the capsule and a geometry which mildly exceeds the dimension of the heating chamber. An embodiment of this functionality is depicted in FIG. 11. The convex shell (202), which serves as an example for a geometry that exceeds the dimension of the heating chamber (81, FIG. 15), is deformed upon insertion of the capsule (1, FIG. 1) into the heating chamber (81) and presses tightly to the sidewalls of the heating chamber (81), maximizing the contact area. Through insertion, lateral forces (93) are exerted on the capsule shell (202).

Figure 12:
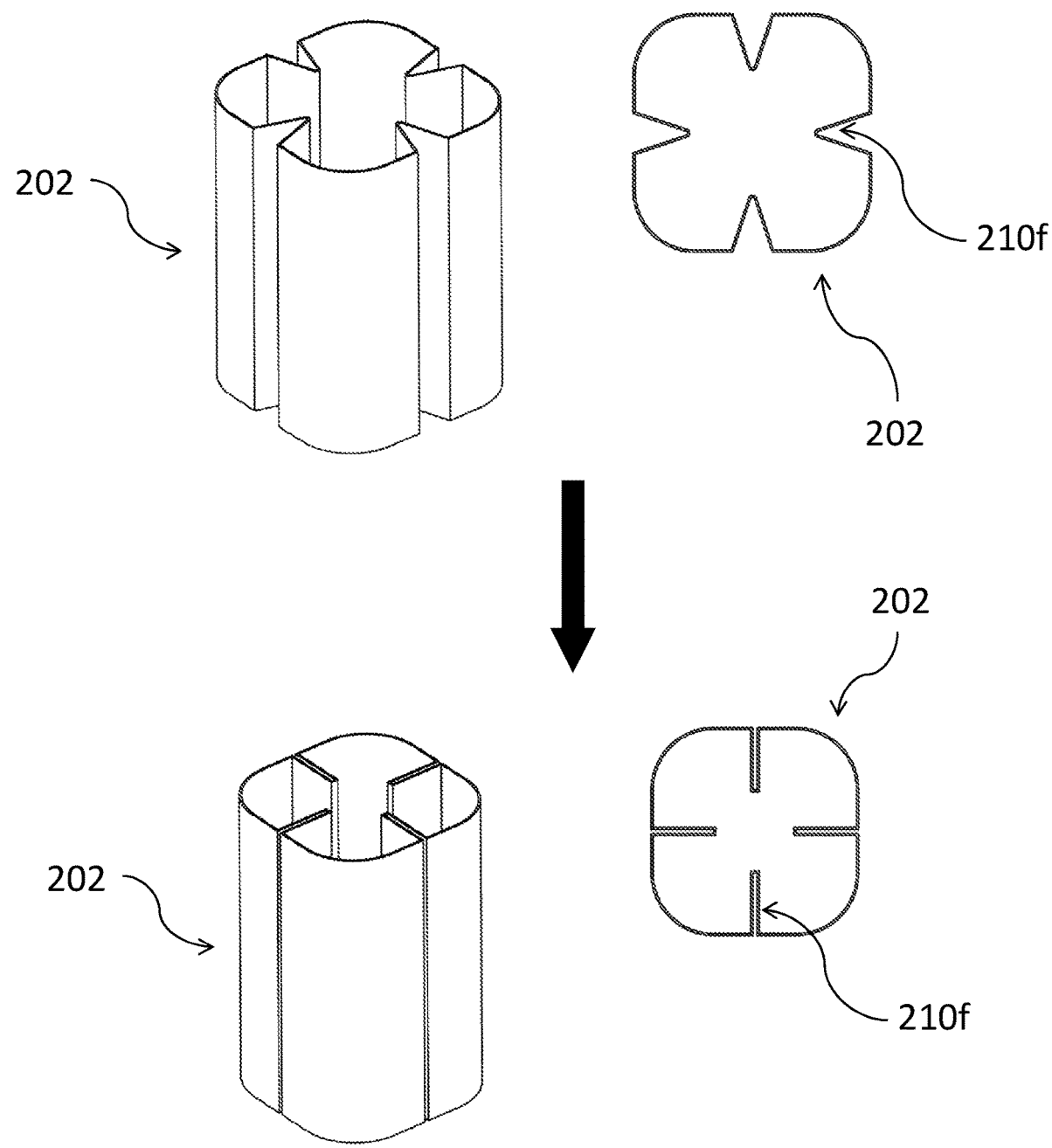
FIG. 12 illustrates an isometric and a top view of the shell (202) before insertion (top of page) and after insertion (bottom), showing the press-fit functionality of the shell with dedicated indentations for deformation upon insertion of the capsule into the heating chamber, in accordance with an embodiment.

The deformed area can be the entire shell (202, FIG. 11) or fractions (210f) of the shell (202). Another embodiment of this functionality, the deformation of a dedicated area (2100 and not the entire shell, is illustrated in FIG. 12. During insertion, the shell (202) deforms at the area of the indentations (2100. Conical shape of the shell (202, FIG. 10) is another example, with which the press-fit can be achieved.

In another embodiment, increased contact area can be achieved with a tight-fit through precise and accurate shaping of the capsule, fitting into the heating chamber without gaps.

Airtightness of the capsule within the heating chamber is essential in order to direct the airflow in the controlled manner, required for the atmospheric pressure drop; leakage flow between the wall of the heating chamber and the shell of the capsule is to be prevented or minimized. This can also be achieved through the press-fit (FIG. 11, FIG. 12), for example. Through deformation of the capsule by insertion, the air path around the capsule is barred and the air exclusively passes through the capsule in the desired manner.

Figure 13:
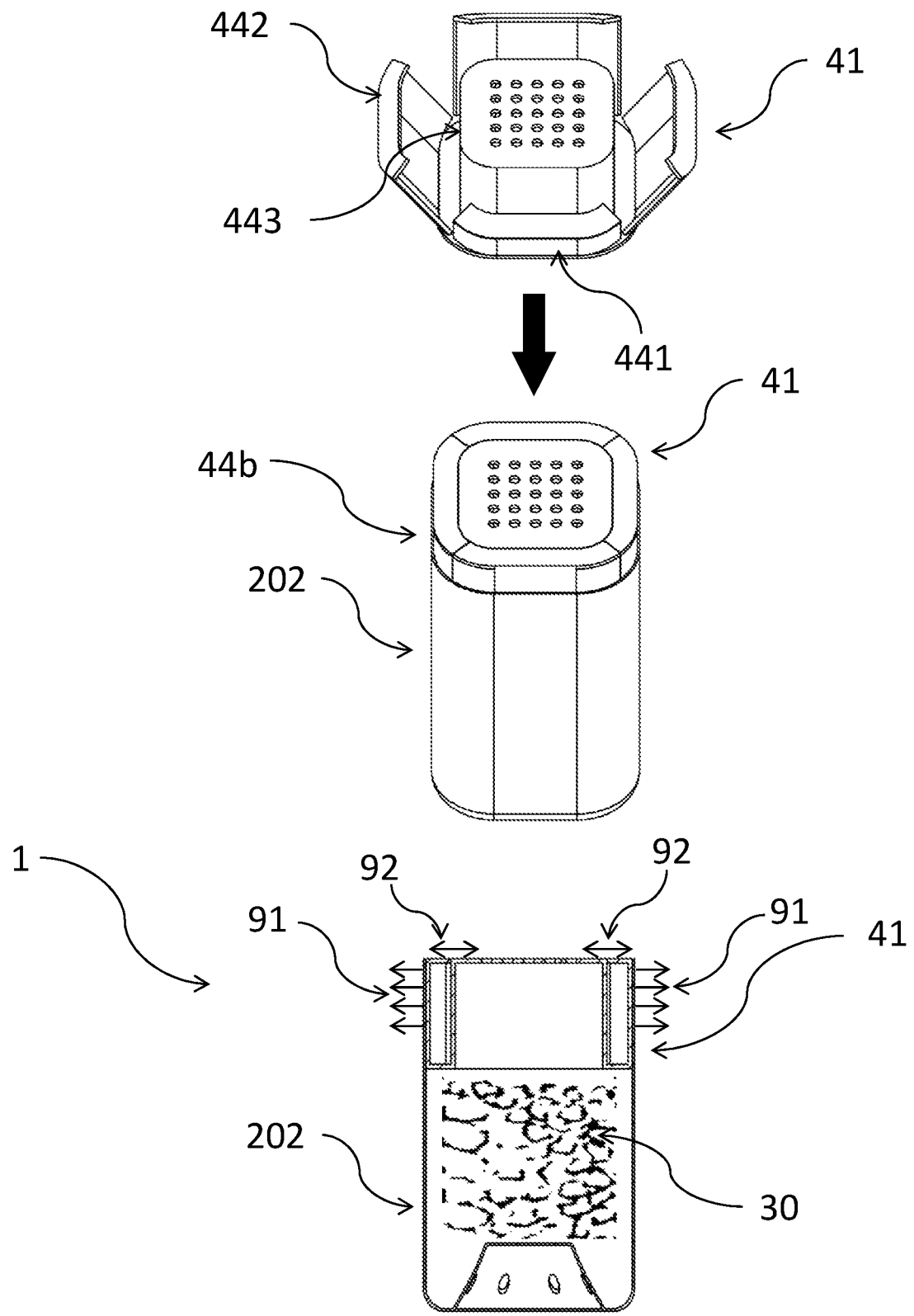
FIG. 13 depicts different views of the capsule, showing the concept of a downstream part (41), which is foldable, on the top of the page the unmounted foldable downstream part (41) can be seen in an isometric view, below the foldable downstream part (41) can be seen in an intermediate state of the mounting (44b) in the shell (202), shown in an isometric view and at the bottom of the page the mounted foldable downstream part (41) is shown in a cross-sectional front view, in accordance with an embodiment.

In an embodiment of the capsule (1), which is illustrated in FIG. 13, the gaps between the shell (202) and the foldable downstream part (41, FIG. 9) as well as the gaps between the capsule (1) and the heating chamber (81, FIG. 15) of the vapor producing device can be sealed simultaneously. After filling the capsule (1) with the herbal product (30), the unmounted downstream part (41), which is foldable, can be mounted into the shell (202). The assembly has two phases. The first phase begins as soon as the sidewalls of the unmounted foldable downstream part (441) establish contact with the shell (202). During this phase, the sidewalls of the foldable downstream part (441) are being pushed inwards by the shell (202). The second phase begins as soon as the top edges of the sidewalls of the foldable downstream part (442) reach the core walls of the foldable downstream part (443). These parts are designed in a way that phase two will start before the foldable downstream part (41) is completely mounted into the shell (202), representing an intermediate state of the foldable downstream part mounting (44b). During the second phase, the more the downstream part (41), which is foldable, is pushed into the shell (202), the more tension (92) will be generated between the top edges of the sidewalls of the foldable downstream part (442) and the core walls of the foldable downstream part (443); this tension exerts lateral forces (91) in all directions between the mounted downstream part (41), which is foldable, and shell (202) which cause the sealing functionality of the mounted foldable downstream part (41) both with the heating chamber (81, FIG. 15) of the vapor producing device and between the mounted foldable downstream part (41) and the shell (202).

Figure 14:
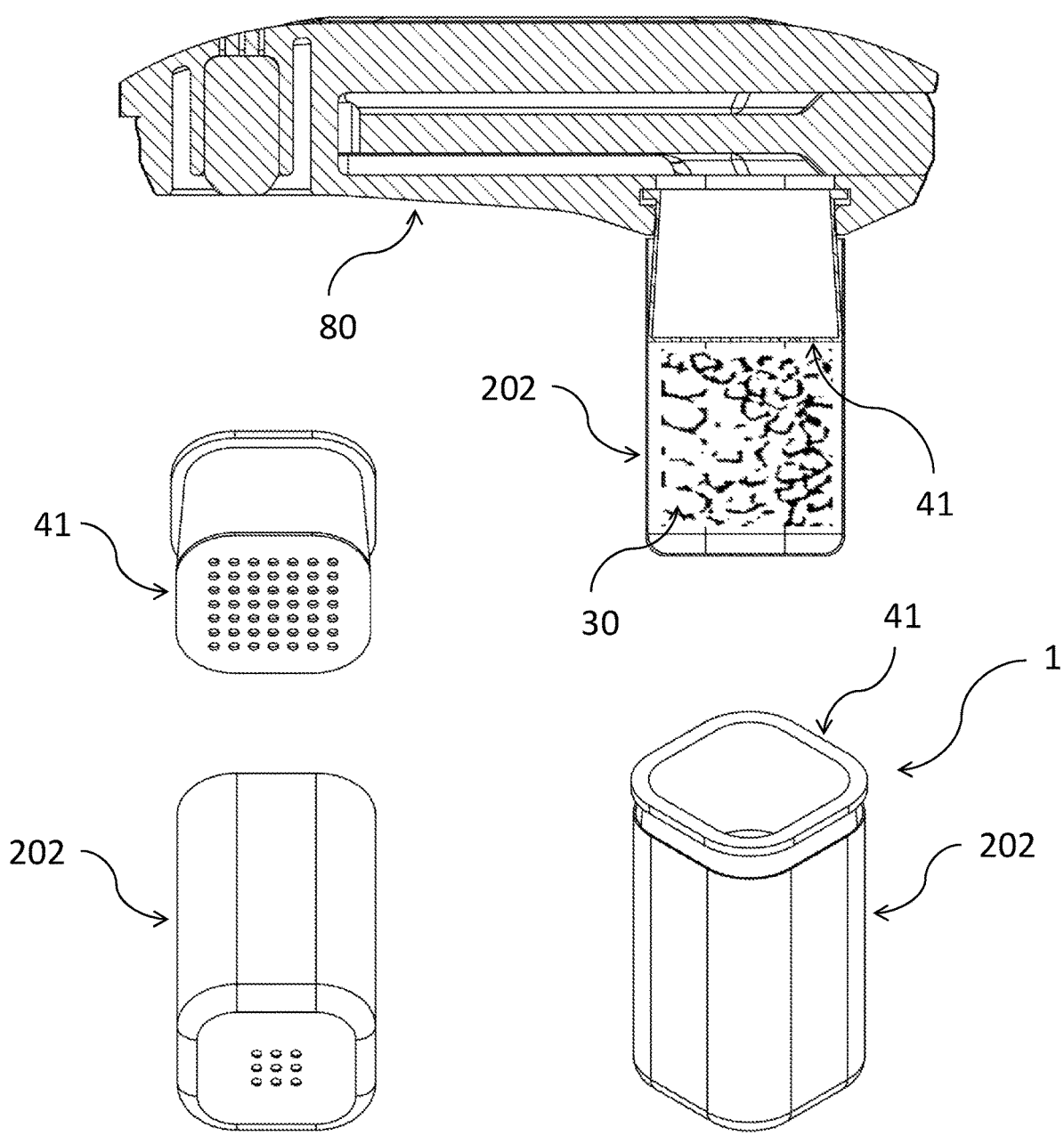
FIG. 14 presents different views of the capsule (1), showing the concept of a downstream part (41), which is elongated, for insertion into the mouthpiece of the vapor producing device (80), in accordance with an embodiment.

Airtightness can also be achieved by use of other geometries of the capsule (1) and mechanisms. In accordance with an embodiment, an elongated downstream part (41) and shell (202) are illustrated in FIG. 14. A long capsule (1), that can slide or be inserted into the mouthpiece of the vapor producing device (80) with an airtight fit, can be used to avoid leakage flow. A downstream part (41), which is elongated, ensures to keep the herbal product (30) in the appropriate position with respect to the heating chamber of the vapor producing device (81, FIG. 15). This is beneficial in terms of consistent vaporization of the entire herbal product (30) because the heat transfer to the herbal product (30) above the boundaries of the heating chamber (81) based on conduction is less homogenous. The feasibility of this approach depends on the making of the mouthpiece (80) and the materials used; elastic materials, such as silicone rubber, will allow for an airtight fit, preventing leakage. Solely for configurations establishing an airtight connection between the mouthpiece (80) and the capsule (1), the capsule (1) does not need to tightly press to the walls of the heating chamber (81) in order to accomplish airtightness and a controlled air pathway. Even though this is beneficial in terms of efficient heat transfer to the herbal product (30).

Another way to ensure the airtightness of the capsule within the heating chamber is through use of a flexible downstream part, which serves as a spring, closing the gaps between the heating chamber wall and the capsule.

Figure 15:
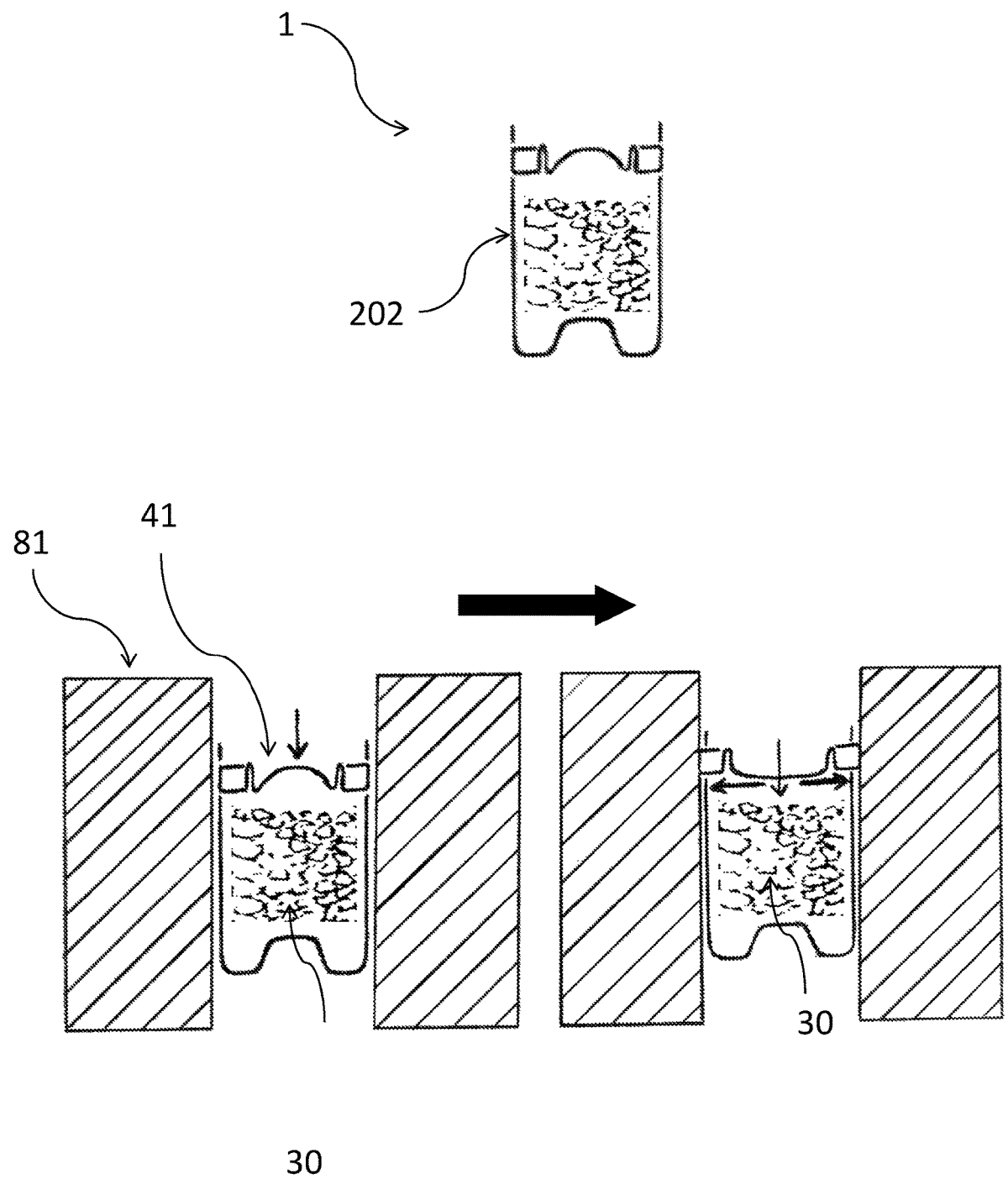
FIG. 15 shows two cross-sectional front views of the capsule (1) when inserted in the heating chamber (81), illustrating the click-locking functionality of the downstream part (41) for clamping to the heating chamber (81), in accordance with an embodiment.

The capsule (1) may be clamped within or inserted into the heating chamber (81) through a click-locking mechanism illustrated in FIG. 15, in accordance with an embodiment. The click-locking mechanism is engaged after insertion of the capsule (1) through downwards pushing of the top surface of the downstream part (41). The vertical force exerted on the capsule (1) after insertion causes the convex downstream part (41) to transition into an engaged concave position. The tension required for this mechanism is achieved through the elasticity of the material. The lateral tension, which is generated through the engagement, aligns and fixes the shell (202) of the capsule (1) within the heating chamber (81). Correct positioning of the capsule (1) is crucial since airflow can be altered by misalignment, diminishing the efficiency of the system for vapor production.

The positioning of the downstream part in the shell is essential in order to have controlled airflow inside the capsule. Furthermore, a rigid connection between these parts is necessary for removal of the capsule from the heating chamber after use. This rigid connection can be achieved through various joining techniques, including press-fitting, gluing/bonding, welding, seaming, snap-fitting or any other suitable joining technique. Preferably, the shell (202) and the downstream part (41) are rigidly connected, more preferably by press-fitting, gluing, bonding, welding, seaming or snap-fitting. Also, the shell (202) and the downstream part (41) and/or the upstream part (40) can be rigidly connected, preferably by press-fitting, gluing, bonding, welding, seaming or snap-fitting.

Figure 16:
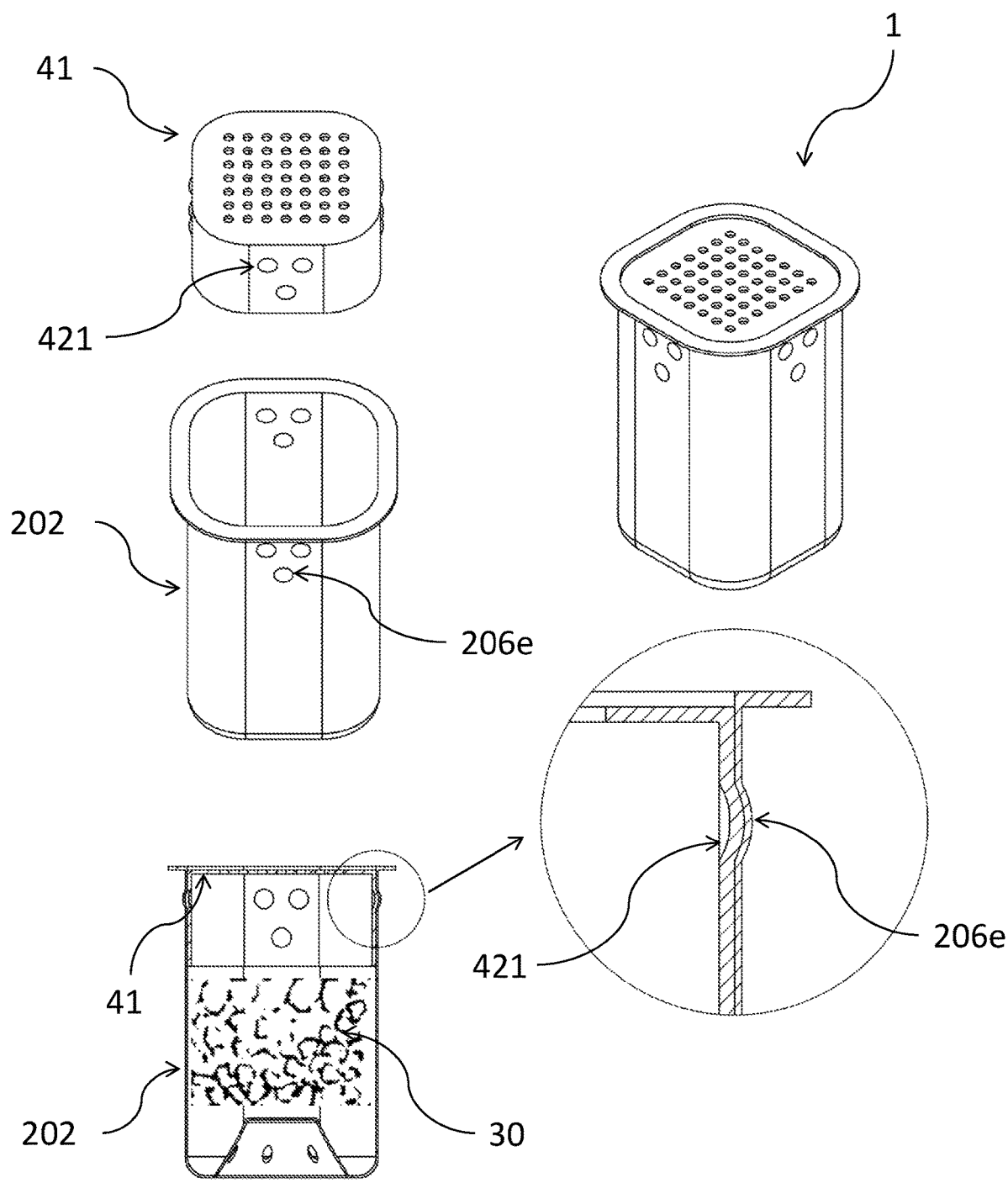
FIG. 16 shows different views of the capsule (1) illustrating the snap-fit functionality of the snap-fit downstream part (41) with the snap-fit shell (202), in accordance with an embodiment.

An embodiment for implementing the joining functionality in form of a snap-fit of the capsule (1) is shown in FIG. 16, where the downstream part (41) is mounted into the shell (202) through a snap-fit functionality in order to close the capsule (1) after filling with the herbal product (30). During mounting of the snap-fit downstream part (41) into the snap-fit shell (202), the indents of the snap-fit downstream part (421) slide into the indents of the snap-fit shell (206e) as soon as the downstream part (41) reaches the intended position in the shell (202).

Figure 17:
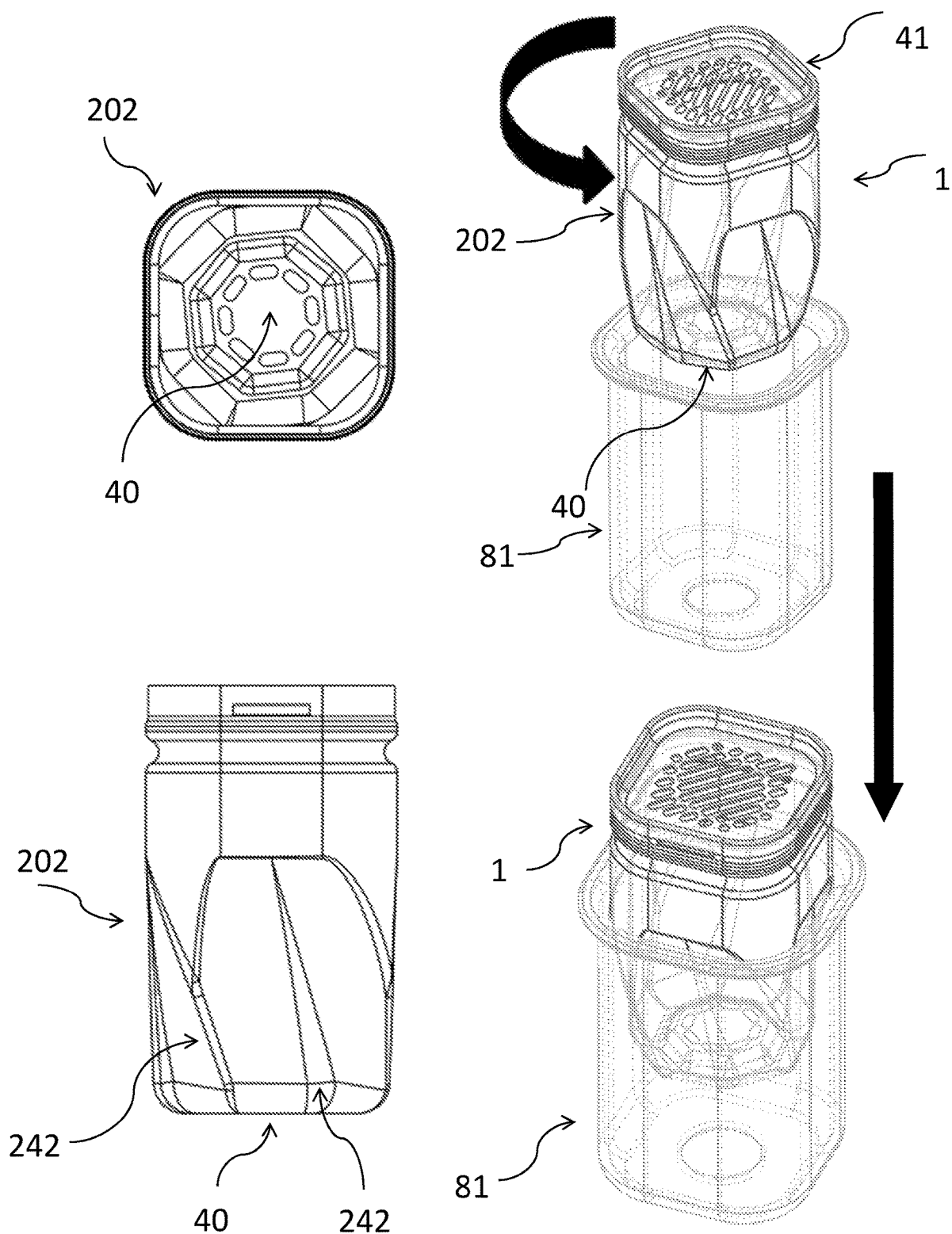
FIG. 17 illustrates a top view of the shell (202) with the upstream part (40) (top left of page), a front view of the shell (202) with the upstream part (40) (bottom left of page) and an isometric view of a self-aligning capsule (1) (upstream part (40), shell (202), downstream part (41)) before and after insertion into a heating chamber (81) (right of page), in accordance with an embodiment.

For convenient, airtight and straightforward insertion of the capsule (1, FIG. 1) into the vapor producing device a self-aligning design can be applied. More specifically, the capsule (1) may be inserted into the heating chamber (81) through a self-aligning mechanism. An embodiment of this capsule (1) with self-aligning mechanism is depicted in FIG. 17. The upstream part (40) and/or the shell (202) are configured in a way, that the self-aligning capsule (1), comprising an upstream part (40), a shell (202) and a downstream part (41), slides into its intended position within the heating chamber (81) of the vapor producing device without getting stuck through inadequate insertion. Capsules (1) with self-aligning functionality can have any capsule shape, or geometry of the upstream part (40) and/or the shell (202) that exhibit self-aligning structures, such as self-aligning edges (242) or self-aligning curvatures that aid to guide, or automatically guide the capsule (1) into the intended position within the heating chamber (81), regardless of the insertion orientation, if the self-aligning capsule (1) is inserted with the upstream part (40) or the shell (202) first. Misaligned insertion may damage the capsule and/or stuck capsules may be inconvenient for the user, which can be prevented through the self-aligning capsules. Misaligned capsules may change the airflow, which impacts the efficacy of vaporization.

Figure 18:
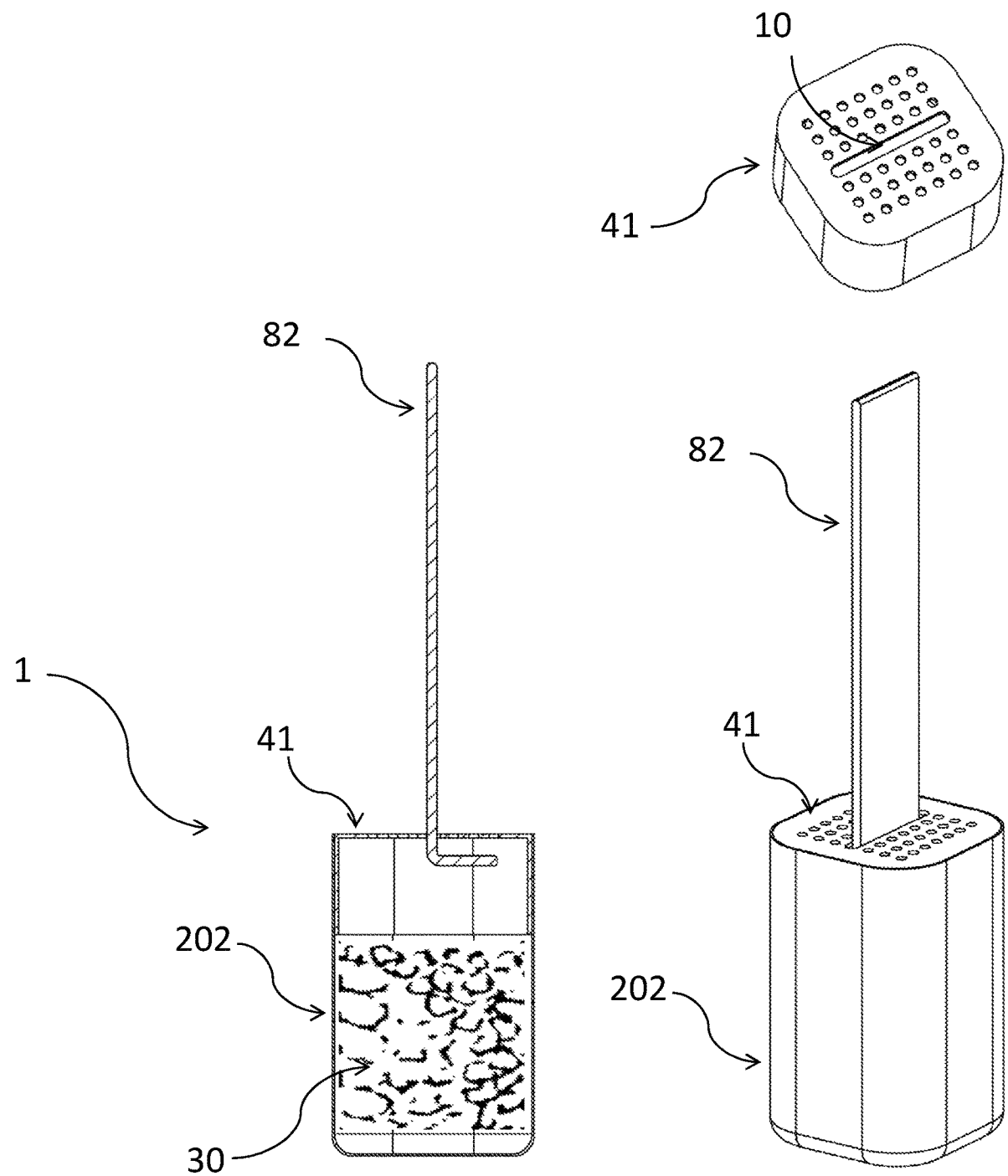
FIG. 18 presents a cross-sectional front (left of page) and an isometric view of the capsule (bottom right of page), as well as an isometric view of a downstream part (41) with a multitude of circular perforations (10) and a slit-shaped perforation (10) (top right of page), showing a functionality for pulling the capsule out of the heating chamber by means of a lever (82), in accordance with an embodiment.

Ease of removal of the capsule (1) from the vapor producing device after use and consumption of the herbal product (30, FIG. 18) is essential. In accordance with an embodiment, a mechanism for removal of the capsule (1) is shown in FIG. 18. This can be achieved through a slit-shaped perforation (10) in the downstream part (41), which is connected to the shell (202). A thin lever (82) can be mated or inserted into the perforation (10) in order to pull out the capsule (1). The pull functionality can be achieved with alternative concepts. The capsule (1) may carry flaps, rings, or levers that may either be part of the capsule (1) or that are attached to the capsule (1) for the purpose of removal of the capsule (1) after use. Any other suitable member may also be used for this purpose.

Information about the content and the shelf life of the capsule can be given on the exterior of the shell, or any other suitable position, including the packaging.

EXPERIMENTS

Figure 19:
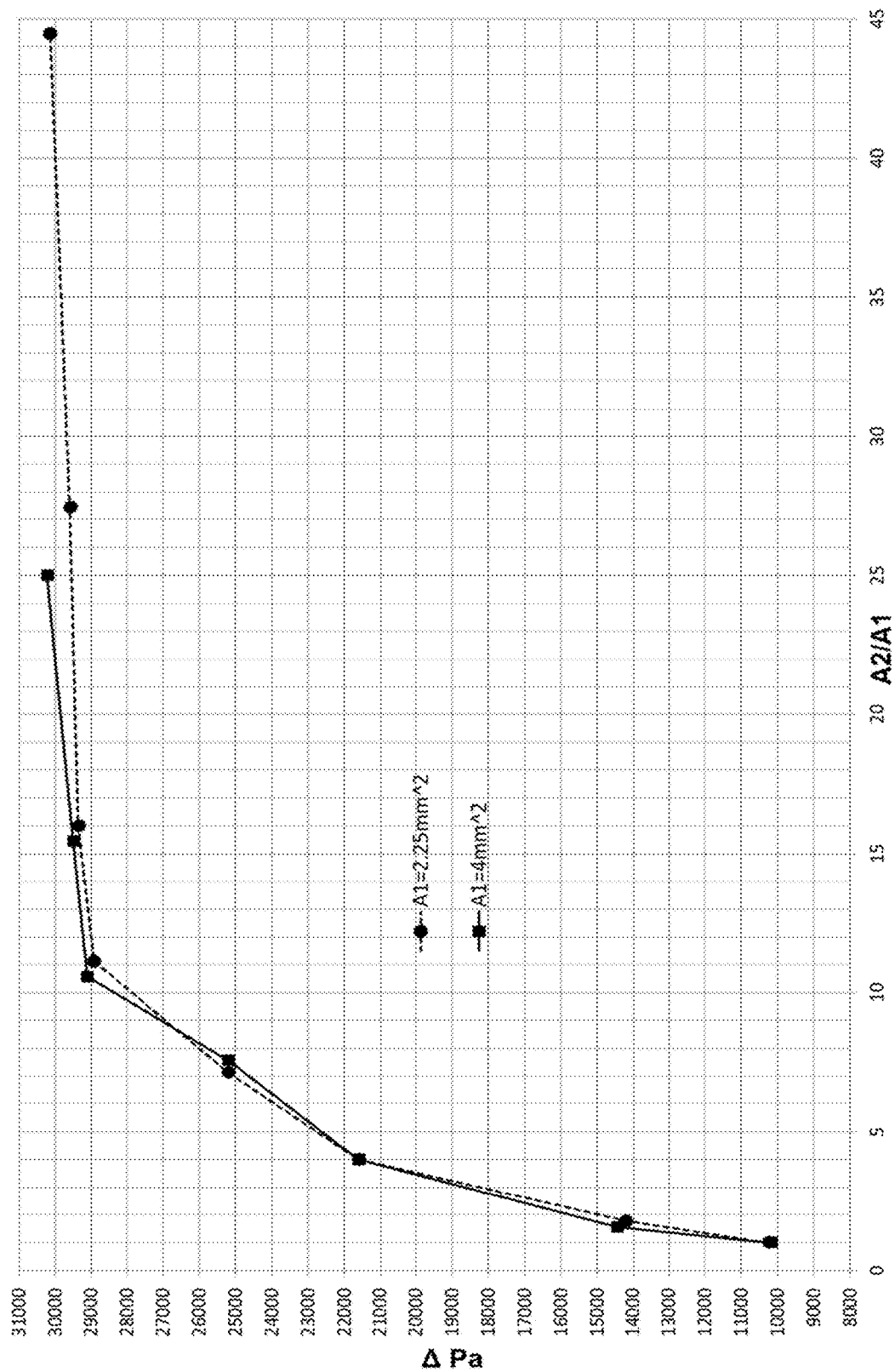
FIG. 19 shows the results of a calculation of the atmospheric pressure reduction within the capsule through inhalation as shown in table 1. In two graphs Δ Pa is plotted against the ratio A2/A1.

The atmospheric pressure reduction or atmospheric pressure drop was numerically calculated as a function of the ratio of the flow-through-area A2 of the outlet orifice over the flow-through-area A1 of the inlet orifice for two exemplary flow-through-areas A1 with an area of 2.25 mm$^2$ and 4 mm$^2$, respectively, for the steady state. The reduced atmospheric pressure which can be achieved with the lungs was set at 70,000 Pa for this calculation (from an initial atmospheric pressure of 101,325 Pa), which is well within the physiological boundaries for human lungs; this pressure of 70,000 Pa is denoted as Pa$_{lung}$. The atmospheric pressure reduction. which was calculated here, is the effective reduction of the atmospheric pressure in the capsule volume in compassion to the initial atmospheric pressure through the inhalation process. Considering Pa$_{lung}$, a maximum value of 31,325 Pa could be reached for the atmospheric pressure reduction in these examples. Since the volume of the capsule, which is the internal volume of the capsule, is small in comparison to the volume of an inhalation draw, the steady state was assumed; the lag time until the steady state was reached is negligible under the chosen conditions. More specifically, for the calculation, the test capsule volume was 1.6 cm$^3$, which is the internal volume of a cuboid with the dimension 10×10×16 mm. The test capsule volume was chosen under considering of the geometry and volume of the heating chambers of common vapor producing devices, in fact, many vapor producing devices have heating chambers with a smaller internal volume. The pressures are given as the average pressure within the test capsule volume. The results are compiled in table 1, the results are additionally plotted in FIG. 19. The atmospheric pressure reduction which is denoted as Δ Pa in table 1 and FIG. 19 reached a plateau of approx. 30,000 Pa at the ratio A2/A1 of approx. 10 and bigger values. This means that at a ratio A2/A1 of approx. 10 and bigger values with the chosen conditions, the pressure in the capsule was close to 70,000 Pa, the reduced atmospheric pressure achieved with the lungs Pa$_{lung}$. The initial atmospheric pressure of 101,325 Pa was reduced by approx. 30,000 Pa through the restriction of the inlet flow-through-area A1 in comparison to the outlet flow-through-area A2 for ratios of A2/A1 of 10 and bigger values during inhalation, which is drawing on the vapor producing device with inserted capsule, assuming airtightness of the system.

TABLE 1

| A1 = 2.25 mm$^2$ | | A1 = 4 mm$^2$ | |
| --- | --- | --- | --- |
| A2/A1 | Δ Pa | A2/A1 | Δ Pa |
| 1 | 10.258 | 1 | 10.183 |
| 1.78 | 14.206 | 1.56 | 14.455 |
| 4 | 21.619 | 4 | 21.619 |
| 7.1111 | 25.194 | 7.56 | 25.194 |
| 11.111 | 28.932 | 10.56 | 29.115 |
| 16 | 29.357 | 15.44 | 29.493 |
| 27.444 | 29.592 | 25 | 30.219 |
| 44.444 | 30.139 | | |

The invention claimed is:
1. A capsule for use in a vapor producing device comprising a battery, the capsule being filled with a herbal product and comprising:

a shell;
an upstream part; and
a downstream part, wherein an inlet orifice configured for receiving air during an inhalation process is in one or both of the upstream part and the shell, and an outlet orifice configured for receiving air during the inhalation process is in the downstream part, the inlet orifice and the outlet orifice comprising a multitude of perforations; and
an internal volume defining a space between the inlet orifice and the outlet orifice configured for air to move between each perforation associated with the inlet orifice and each perforation associated with the outlet orifice, wherein a flow-through-area A2, being a combined surface area of the perforations of the outlet orifice, is larger than a flow-through-area A1, being a combined surface area of the perforations of the inlet orifice, wherein a ratio between the flow-through-area A2 and the flow-through-area A1 is from 1.5:1 to 12:1 for reducing battery usage required to reach a temperature at which vaporization takes place, and wherein an air pressure reduction occurs during the inhalation process as a function of a ratio of the flow-through-area A2 of the outlet orifice over the flow-through-area A1 of the inlet orifice.

2. The capsule according to claim 1, wherein a perforation diameter in at least one of the upstream part, the downstream part and the shell is at least 10% smaller than an average particle size of the herbal product.

3. The capsule according to claim 1, wherein at least one of the shell, the upstream part and the downstream part consists of an impermeable material.

4. The capsule according to claim 1, wherein at least one of the shell, the upstream part and the downstream part comprise a deformable material, preferably aluminum, aluminum alloys, stainless-steel alloys, titanium, titanium alloys, copper, copper alloys, plastics, high-performance plastics, paper, hemp or compressed herbal product or combinations thereof.

5. The capsule according to claim 1, wherein at least one of the shell and the downstream part and the upstream part are rigidly connected, preferably by press-fitting, gluing, bonding, welding, seaming or snap-fitting.

6. The capsule according to claim 1, wherein the shell has a conical or convex shape.

7. The capsule according to claim 1, wherein the capsule contains membranes.

8. The capsule according to claim 1, wherein the capsule carries separators, which are preferably part of the shell or a separate part.

9. The capsule according to claim 1, wherein the capsule carries seals.

10. The capsule according to claim 1, wherein the capsule has a flange.

11. The capsule of claim 1, wherein the upstream part comprises nine holes in a three-by-three grid configuration.

12. The capsule of claim 1, wherein the upstream part comprises twenty-five holes in a five-by-five grid configuration.

13. The capsule of claim 1, wherein the upstream part comprises forty-nine holes in a seven-by-seven grid configuration.

14. The capsule of claim 1, wherein the downstream part comprises forty-nine holes in a seven-by-seven grid configuration.

15. A vapor producing device comprising a capsule wherein the capsule is filled with a herbal product and comprising a shell, an upstream part and a downstream part, wherein an inlet orifice is in one or both of the upstream part and the shell, and an outlet orifice is in the downstream part, the inlet orifice and the outlet orifice comprising a multitude of perforations,
and wherein a flow-through-area A2, being a combined surface area of the perforations of the outlet orifice, is larger than a flow-through-area A1, being a combined surface area of the perforations of the inlet orifice, wherein a ratio between the flow-through-area A2 and the flow-through-area A1 is from 1.5:1 to 12:1 for reducing battery usage required to reach a temperature at which vaporization takes place wherein the vapor producing device further comprises an internal volume defining a space between the inlet orifice and the outlet orifice configured for air to move between each perforation associated with the inlet orifice and each perforation associated with the outlet orifice, and wherein a pressure reduction occurs during the inhalation process as a function of a ratio of the flow-through-area A2 of the outlet orifice over the flow-through-area A1 of the inlet orifice.

16. A method of using a capsule, the method comprising: using a capsule in a vapor producing device comprising a battery, the vapor producing device comprising a heating chamber with sidewalls, wherein the capsule is inserted airtight into the vapor producing device and preferably the shell is pressed tightly to the sidewalls of the heating chamber; wherein the capsule is filled with a herbal product and comprising a shell, an upstream part and a downstream part, wherein an inlet orifice is in one or both of the upstream part and the shell, and an outlet orifice is in the downstream part, the inlet orifice and the outlet orifice comprising a multitude of perforations, and wherein a flow-through-area A2, being a combined surface area of the perforations of the outlet orifice, is larger than a flow-through-area A1, being a combined surface area of the perforations of the inlet orifice, wherein a ratio between the flow-through-area A2 and the flow-through-area A1 is from 1.5:1 to 12:1 for reducing battery usage required to reach a temperature at which vaporization takes place and wherein a pressure reduction occurs during the inhalation process as a function of a ratio of the flow-through-area A2 of the outlet orifice over the flow-through-area A1 of the inlet orifice.

17. The method of claim 16, wherein the capsule is inserted into the heating chamber through a click-locking mechanism, or through a self-aligning mechanism.

18. The method of claim 16, wherein the vapor producing device is a portable vapor producing device.

* * * * *